US012106239B1

(12) United States Patent
Perry et al.

(10) Patent No.: US 12,106,239 B1
(45) Date of Patent: Oct. 1, 2024

(54) SYSTEMS AND METHODS FOR AUTOMATED AND CENTRALIZED EVENT DETECTION AND FACILITY COMMUNICATION

(71) Applicant: TeleTracking Technologies, Inc., Pittsburgh, PA (US)

(72) Inventors: Thomas Perry, DuBois, PA (US); Steven P. Gaghan, Mars, PA (US); Benjamin Joel Martin, Harmony, PA (US); Raymond C. Lantz, Pensacola, FL (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 0 days.

(21) Appl. No.: 17/576,450

(22) Filed: Jan. 14, 2022

Related U.S. Application Data

(63) Continuation of application No. 15/335,622, filed on Oct. 27, 2016, now Pat. No. 11,238,380, which is a
(Continued)

(51) Int. Cl.
*G06Q 10/0631* (2023.01)
*G06F 3/0482* (2013.01)
*G06F 3/14* (2006.01)

(52) U.S. Cl.
CPC ... *G06Q 10/063112* (2013.01); *G06F 3/0482* (2013.01); *G06Q 10/06311* (2013.01);
(Continued)

(58) Field of Classification Search
CPC ... G06Q 10/063112; G06Q 10/063114; G06Q 10/06311; G06Q 10/063116; G06F 3/0482; G06F 3/14
(Continued)

(56) References Cited

U.S. PATENT DOCUMENTS 7,881,957 B1 * 2/2011 Cohen ............... G06Q 30/08
8,260,736 B1 9/2012 Lear et al.
(Continued)

OTHER PUBLICATIONS

I-Sector Introduces Work Flow Manager Application for Cisco Telephony, FinancialWire, Forest Hills, Jul. 28, 2004, 2 pages.
(Continued)

*Primary Examiner* — Charles Guiliano
(74) *Attorney, Agent, or Firm* — FERENCE & ASSOCIATES LLC

(57) ABSTRACT

Systems and methods are provided for automatically assigning a task identified from information received from one or more sensors. The automatically assigning including identifying a plurality of matches between the task and more than one of the plurality of individuals based on attributes of the individuals and requirements of the task; and in response to identifying a match, automatically assigning the task to the individual corresponding to a match having a highest ranking, wherein the automatically assigning comprises displaying the task on the display within the mobile application associated with the individual. Additionally, the systems and methods may determine one or more additional tasks that are related to the task and automatically assigning the one or more additional tasks to one or more individuals.

20 Claims, 12 Drawing Sheets

Related U.S. Application Data continuation-in-part of application No. 14/731,190, filed on Jun. 4, 2015, now Pat. No. 10,235,646.

(60) Provisional application No. 62/145,984, filed on Apr. 10, 2015.

(52) U.S. Cl.
CPC ............... G06Q 10/063114 (2013.01); G06Q 10/063116 (2013.01); G06F 3/14 (2013.01)

(58) Field of Classification Search
USPC ......................................................... 705/7.14
See application file for complete search history.

(56) References Cited

U.S. PATENT DOCUMENTS

| | | |
|---|---|---|
| 2006/0167738 A1 | 7/2006 | Spear et al. |
| 2007/0100677 A1 | 5/2007 | Boss et al. |
| 2007/0194939 A1 | 8/2007 | Alvarez et al. |
| 2008/0164998 A1* | 7/2008 | Scherpbier ............. G16H 40/20 340/539.13 |
| 2009/0284348 A1 | 11/2009 | Pfeffer |
| 2009/0313046 A1 | 12/2009 | Badgett et al. |
| 2011/0314402 A1 | 12/2011 | Kikin-Gil et al. |
| 2012/0173688 A1 | 7/2012 | True et al. |
| 2012/0278681 A1 | 7/2012 | True et al. |
| 2013/0197957 A1 | 8/2013 | Nudd et al. |
| 2013/0204633 A1* | 8/2013 | Jourdan ................. G16H 40/20 705/2 |
| 2013/0275187 A1 | 10/2013 | Patel |
| 2014/0278681 A1 | 9/2014 | Cox et al. |

OTHER PUBLICATIONS

I-Sector Introduces Work Flow Manager Application for Cisco Telephony, FinancialWire, Jul. 2010, 3 pages.
The Support Services Suite: System Administration and User's Guide, TeleTracking Technologies, 2006, 229 pages.
Service Tracking Application: System Administration and User's Guide, TeleTracking Technologies, 2011, 215 pages.
Service Tracking Application: Web Requester's Guide, TeleTracking Technologies, 2011, 22 pages.
Service Tracking Application: System Administration and User's Guide, TeleTracking Technologies, 2012, 232 pages.
Service Tracking Application: Web Requester's Guide, TeleTracking Technologies, 2012, 22 pages.

\* cited by examiner

| Created | Status △ | Task ID | Category | Item | Priority | Req Dept | Origin | Destination |
|---|---|---|---|---|---|---|---|---|
| 4/12 4:02 PM | Pending | 150412 | Insert | (1) Central Line | Medium | CPM | 4000-B | -- |
| 4/12 3:54 PM | Pending | 150411 | Consult | -- | Medium | BNM | 4001-A | -- |
| 4/13 2:14 PM | Assigned | 150428 | Deliver | (1) Baristic Bed | Medium | QA | 4000-B | -- |
| 4/13 2:51 PM | Assigned | 150422 | Clean | -- | Medium | mci | Nurses Station | -- |
| 4/15 10:22 AM | Assigned | 150421 | Insert | (2) Infusion Pump | Medium | -- | Nurses Station | -- |
| 4/14 5:16 PM | Assigned | 150418 | Deliver | (1) Infusion Pump | Medium | -- | 4000-B | -- |
| 4/13 6:32 PM | Assigned | 150416 | Clean | -- | High | HERE | Booth | -- |

SYSTEMS AND METHODS FOR AUTOMATED AND CENTRALIZED EVENT DETECTION AND FACILITY COMMUNICATION

CROSS REFERENCE TO RELATED APPLICATIONS

This application claims priority to co-pending U.S. patent application Ser. No. 15/335,622, filed on Nov. 27, 2016, titled "Systems and Methods for Automated and Centralized Event Detection and Facility Communication," which is a continuation-in-part and claims priority to U.S. patent application Ser. No. 14/731,190, filed Jun. 4, 2015, titled "Systems and Methods for Automated and Centralized Event Detection and Facility Communication," which claims priority from U.S. Provisional Application Ser. No. 62/145,984, filed on Apr. 10, 2015, titled "Systems and Methods for Automated and Centralized Event Detection and Facility Communication," the contents of all of which are incorporated by reference herein.

BACKGROUND

Modern hospitals treat hundreds of patients every day. In addition to the doctors and nurses caring for patients, there are many departments and support staff teams that support the infrastructure of the hospital assigned to ensure that rooms are clean, equipment is sanitized and in working condition, and that people and items are moved to the right place at the right time.

Traditional systems are largely telephone-based, in which a requester places a telephone call to a centralized phone number, and requests a service or provides information about a status. The requester may speak with a computerized interactive voice response (IVR) system. The IVR system then processes the received information for review by a dispatcher to identify and direct a responder in response to the requester's information. Current systems rely solely on information received during a manual telephone call, which can be sporadic and/or untimely, and can include incorrect information.

Because traditional systems rely on telephone calls and IVR-based processing, traditional systems often experience very high call volumes which strain communication networks in the facility. In many instances, unnecessary and redundant calls also increase network strain.

In view of the deficiencies and drawbacks of current systems and the technical problems discussed above, improved systems and methods for automated facility communication is desired.

BRIEF SUMMARY

Disclosed embodiments relate to automated communications in a facility using real-time data collection from one or more sensors or networked scheduling databases, and employing one or more communication networks to generate and transmit notifications and messages regarding events associated with the collected data. In some embodiments, the facility may include a medical facility, hotel, or any other type of facility that benefits from centralized communication and dispatch systems.

Disclosed embodiments address the technical problems discussed above through the use of a centralized server that dynamically and automatically queries networked databases and networked sensor devices located throughout the facility to obtain real-time data such as real-time location of the sensor device. Thus, the disclosed embodiments provide a combination and arrangement of computerized hardware in conjunction with ordered combinations of steps in a particular application. As a result, the disclosed embodiments can reduce network strain by dramatically reducing the need for phone calls from requesters by collecting data dynamically as it is needed and by generating and sending messages to provide status updates. In some embodiments, phone calls may be eliminated entirely and replaced with interactive graphical user interfaces on handheld smart devices, to provide a more uniform and accurate way of communicating information. Additionally, the disclosed embodiments provide interactive graphical user interfaces to facilitate easier data input into to the centralized server regarding an event or tasks associated with a detected event.

As discussed below, the disclosed embodiments may improve response time, streamline communications between departments in a facility, and provide for intelligent automated communications to send targeted messages to different departments and devices based on a multitude of factors such as attributes or requirements associated with an event, and attributes associated with equipment or individuals related to the event.

Consistent with the present embodiments, a system is disclosed, for centralized event monitoring and notification. The system may comprise a first mobile device associated with a first individual, and a central communication server. The centralized communication server may comprise a memory storing instructions, and at least one processor. The at least one processor may be configured to execute the stored instructions to receive monitoring information indicative of an event, analyze the received monitoring information and data retrieved from at least one networked database about the first individual, select, based on the analysis, the first mobile device for notification about the event, generate notification information for displaying a graphical user interface associated with the event and instructions associated with the event, and transmit, via a wireless network, the generated notification information to the first mobile device. The first mobile device may be configured to receive the generated notification information, and provide for display a graphical user interface about the event and the instructions associated with the event.

Consistent with the present embodiments, a method is disclosed. The method may be performed by a central communication server, and may comprise receiving monitoring information indicative of an event, analyzing the received monitoring information and data retrieved from at least one networked database about a first individual, selecting, based on the analysis, the first mobile device for notification about the event, generating notification information for displaying a graphical user interface associated with the event and instructions associated with the event, and transmitting, via a wireless network, the generated notification information to a first mobile device. The first mobile device may be associated first individual and is configured to receive the generated notification information, and provide for display a graphical user interface about the event and the instructions associated with the event.

Consistent with other disclosed embodiments, non-transitory computer-readable storage media may store program instructions, which are executed by at least one processor device and perform any of the methods described herein.

The foregoing general description and the following detailed description are exemplary and explanatory only and are not restrictive of the claims.

BRIEF DESCRIPTION OF THE SEVERAL VIEWS OF THE DRAWINGS

The accompanying drawings, which are incorporated in and constitute a part of this specification, illustrate several embodiments and, together with the description, serve to explain the disclosed principles. In the drawings:

FIG. 8 is an illustration of an example of a task creation interface, consistent with embodiments of the present disclosure.

FIG. 9 is an illustration of an example of a task assignment interface, consistent with embodiments of the present disclosure.

DETAILED DESCRIPTION

Reference will now be made in detail to exemplary embodiments, examples of which are illustrated in the accompanying drawing and disclosed herein. Wherever convenient, the same reference numbers will be used throughout the drawings to refer to the same or like parts.

Figure 1:
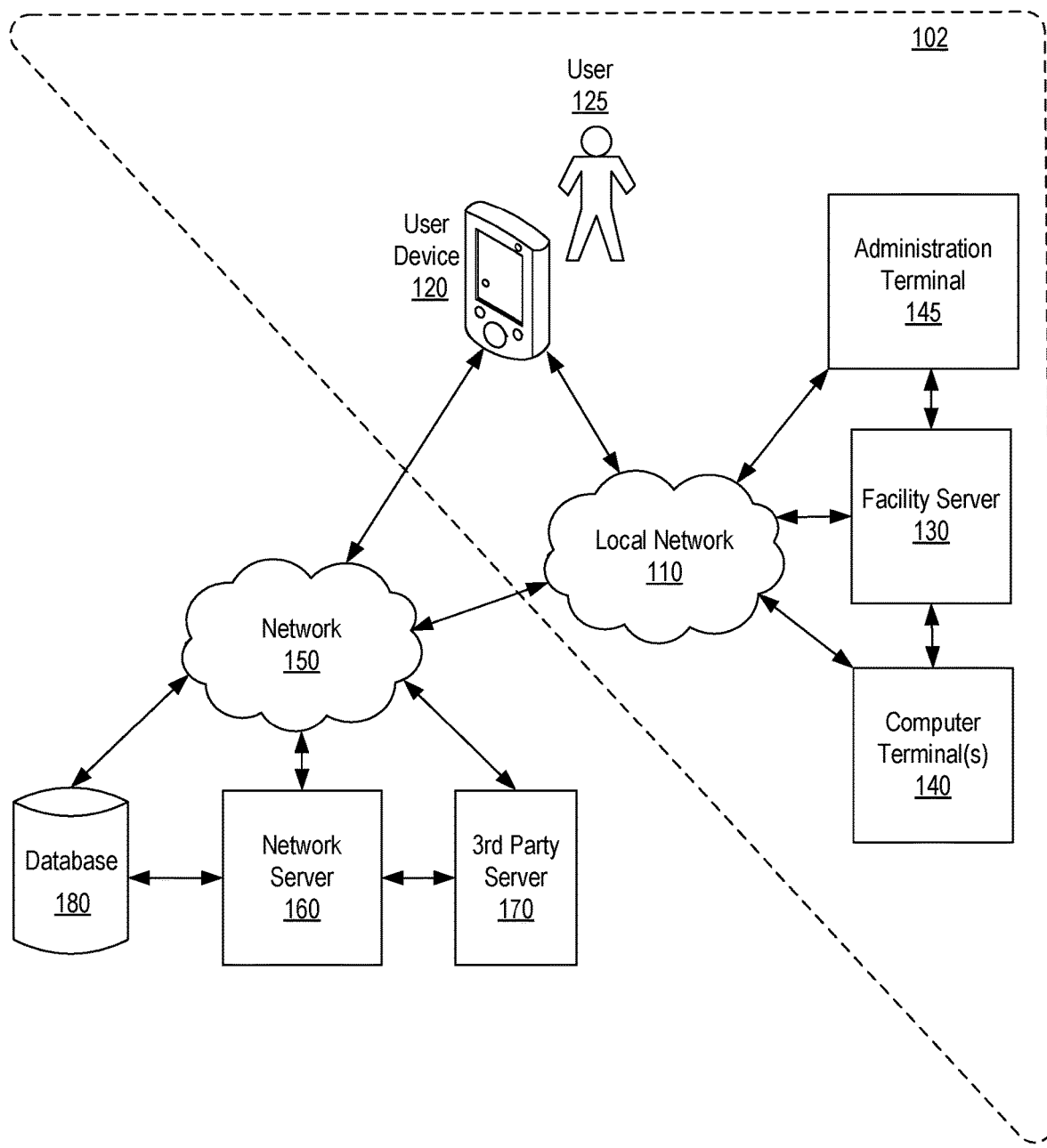
FIG. 1 depicts an example of a system environment for scheduling and managing tasks within an organization, consistent with embodiments of the present disclosure.

FIG. 1 shows a diagram of a workflow automation and management system 100 that may be configured to perform one or more software processes that, when executed by one or more processors, perform methods consistent with disclosed embodiments. The components and arrangements shown in FIG. 1 are not intended to limit the disclosed embodiments, as the components used to implement the disclosed processes and features may vary.

As shown in FIG. 1, workflow automation and management system 100 may include a facility server 130, a computer terminal 140, an administration terminal 145, a user device 120, network server 160, third party server 170, and database 180. The components of system 100 may communicate directly, through network 150, through local network 110, or through a combination of communications methods. In some embodiments, local network 110, facility server 130, computer terminal 140, administrator terminal 145, and user device 120 may be physically disposed within a facility such as a hospital or office building (i.e. as facility system 102) while network 150, network server 160, third party server 170, and database 180 may be external to the workplace. Other components known to one of ordinary skill in the art may be included in system 100 to perform tasks consistent with the disclosed embodiments. For example, in some embodiments, facility system 102 may include one or more sensor devices located throughout the facility to monitor one or more conditions such as occupancy, temperature, humidity, proximity, and other parameters indicative of a status or condition of a room, area, equipment, or supplies. Additionally, in some embodiments facility system 102 may include one or more wireless receivers (not shown) configured to detect one or more wireless sensor or locating tags, to track a location of a tagged item and/or person, or a condition about the tagged item and/or person.

Computer terminal 140 may be a standalone device disposed in an office, a room, an employee station, or an alternative central location in a workplace. In some embodiments, computer terminal 140 may be a desktop or notebook computer, a flat panel or projected display, or any other display. In some embodiments, computer terminal 140 may be associated with a particular room in a facility, such as a particular patient room, hotel room, conference room, or any other type of room. Thus, a message or task request received from a computer terminal 140 may automatically associate the task request or message with the room in which computer terminal 140 is installed.

Administrator terminal 145 may include computer system or device associated with a user 125 that manages or oversees a portion of facility system 102. For example, administrator terminal 145 may comprise a computer system located at a head nurse station, a housekeeping manager's office, or any other department manager's office or station.

User 125 may be an employee in a workplace environment such as a nurse, a technician, or a dispatcher. User 125 may operate computer terminal 140, user device 120, and/or another computer (not shown) to interact with system 100. System 100 may include multiple types of users such as, for example, task requestors, dispatchers, and responders. Task requestors may include one or more individuals who initiate a request for a certain task to be completed, such as a nurse requesting a hospital bed. In some embodiments, dispatchers may include individuals who perform one or more tasks related to assigning requested tasks. In some embodiments, responders may include one or more individuals assigned to the requested tasks, who perform and complete the tasks.

User device 120 may be a personal computing device such as, for example, a general purpose or notebook computer, a mobile device with computing ability, a tablet, smartphone, wearable device such as Google Glass or smart watches, or any combination of these computers and/or affiliated components. In some embodiments, user device 120 may be a computer system or mobile computer device that is operated by user 125. In some embodiments, user device 120 may be associated with a particular individual such as user 125, such that task assignments directed toward user 125 are sent to mobile device 120.

In some embodiments, user device 120 may communicate with facility server 130 and/or network server 160 via direct wireless communication links (not shown), or via a combination of one or more of local network 110 and/or network 150.

Facility server 130 may be operated by a facility such as a hospital, business, retail location, and the like. Facility server 130 may enable communication within a computer-based system including computer system components such as desktop computers, workstations, tablets, hand held computing devices, memory devices, and/or internal network(s)

connecting the components. Thus, in some embodiments facility server 130 may operate as a centralized hub or station for receiving and processing data associated with disclosed methods and techniques, and for generating and sending transmissions associated with disclosed methods and techniques.

Network 150 may comprise any type of computer networking arrangement used to exchange data. For example, network 150 may be the Internet, a private data network, virtual private network using a public network, and/or other suitable connection(s) that enables system 100 to send and receive information between the components of system 100. Network 150 may also include a public switched telephone network ("PSTN") and/or a wireless cellular network.

Local network 110 may comprise any type of computer networking arrangement used to exchange data in a localized area, such as WiFi, Bluetooth, Ethernet, and other suitable short-range connections that enable computer terminal 140 and user device 120 to send and receive information between the components of system 100. In some embodiments, local network 110 may be excluded, and computer terminal 140 and user device 120 may communicate with system 100 components via network 150. In some embodiments, computer terminal 140 and/or user device 120 may communicate with one or more system 100 components via a direct wired or wireless connection.

Network server 160, Third party server 170, and database 180 may be one or more servers or storage services provided by an entity such as a provider of networking, cloud, or backup services. For example, in some embodiments, network server 160 may be associated with a cloud computing service such as Microsoft Azure™ or Amazon Web Services™. In such embodiments, network server 160 may comprise a plurality of geographically distributed computing systems executing software for performing one or more functions of the disclosed methods. Additionally, in some embodiments, third party server 170 may be associated with a messaging service, such as, for example, Apple Push Notification Service, Azure Mobile Services, or Google Cloud Messaging. In such embodiments, third party server 170 may handle the delivery of messages and notifications related to functions of the disclosed embodiments, such as task creation, task assignment, task alerts, and task completion messages and notifications.

In some embodiments, system 100 may include configurations that vary from the example shown in FIG. 1, which illustrates a facility system 102 working in concert with a cloud computing system including network server 160, third party server 170, and database 180. As a first variation, system 100 may include only facility system 102, and thus may exclude cloud computing components such as network server 160, third party server 170, and database 180. In such embodiments, facility system 102 may handle substantially all operations and functions of the present embodiments. As a second variation, system 100 may exclude components of facility system 102 such as facility server 130. In such embodiments, a cloud computing system including network server 160, third party server 170, and/or database 180 may handle some or all computing and message-related functions of the disclosed embodiments.

Figure 2:
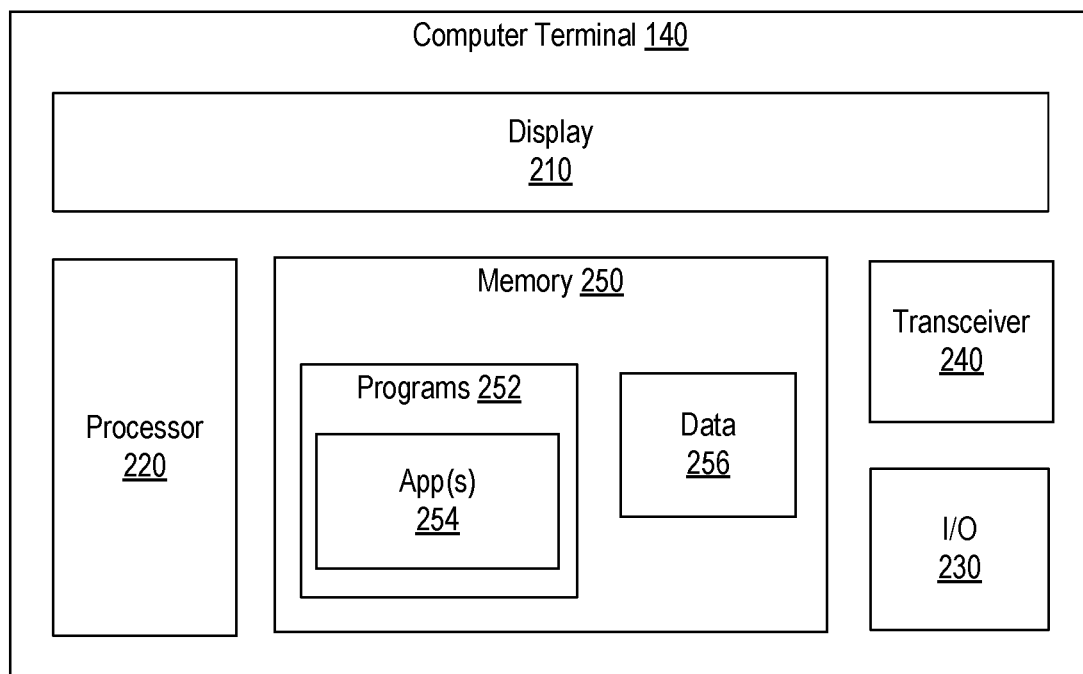
FIG. 2 depicts an example of a computer terminal, consistent with embodiments of the present disclosure.

FIG. 2 shows a diagram of computer terminal 140, consistent with disclosed embodiments. As shown, computer terminal 140 may include a display 210, one or more processors 220, input/output ("I/O") devices 230, a transceiver 240, and memory 250.

Display 210 may include one or more screens for displaying task management information such as, for example, liquid crystal display (LCD), plasma, cathode ray tube (CRT), or projected screens.

Processor 220 may be one or more known processing devices, such as a microprocessors manufactured by Intel™ or AMD™ or licensed by ARM. Processor 220 may constitute a single core or multiple core processors that executes parallel processes simultaneously. For example, processor 220 may be a single core processor configured with virtual processing technologies. In certain embodiments, processor 220 may use logical processors to simultaneously execute and control multiple processes. Processor 220 may implement virtual machine technologies, or other known technologies to provide the ability to execute, control, run, manipulate, store, etc. multiple software processes, applications, programs, etc. In another embodiment, processor 220 may include a multiple-core processor arrangement (e.g., dual, quad core, etc.) configured to provide parallel processing functionalities to allow computer terminal 140 to execute multiple processes simultaneously. One of ordinary skill in the art would understand that other types of processor arrangements could be implemented that provide for the capabilities disclosed herein.

I/O devices 230 may include one or more devices that allow computer terminal 140 to receive input from a user. I/O devices 230 may include, for example, one or more pointing devices, keyboards, buttons, switches, touchscreen panels, cameras, barcode scanners, radio frequency identification (RFID) tag reader, and/or microphones.

Transceiver 240 may include one or more communication modules for establishing communication between computer terminal 140 and other devices of system 100 via, for example, local network 110 and/or network 150. For example, transceiver 240 may include circuitry and one or more antennas for communicating wirelessly with local network 110 using a short range/near-field wireless communication protocol such as Bluetooth™, Bluetooth™ LE, WiFi, and Zigbee. Further, transceiver 240 may communicate with network 150 and/or local network 110 using any known network protocol including any form of wired or wireless internet access.

Memory 250 may include a volatile or non-volatile, magnetic, semiconductor, tape, optical, removable, non-removable, or other type of storage device or tangible (i.e., non-transitory) computer-readable medium that stores one or more program(s) 252, such as app(s) 254, and data 256. Data 256 may include, for example, user information, task information, and display settings and preferences. In some embodiments, data 256 may include one or more rule sets for prioritizing and assigning tasks to one or more employees.

Program(s) 252 may include operating systems (not shown) that perform known operating system functions when executed by one or more processors. By way of example, the operating systems may include Microsoft Windows™, Unix™, Linux™, Apple™ operating systems, Personal Digital Assistant (PDA) type operating systems, such as Microsoft CE™, or other types of operating systems. Accordingly, disclosed embodiments may operate and function with computer systems running any type of operating system. Computer terminal 140 may also include communication software that, when executed by a processor, provides communications with network 150 and/or local network 110, such as Web browser software, tablet, or smart hand held device networking software, etc.

Program(s) 252 may also include app(s) 254, such as a task administration app, which when executed causes computer terminal 140 to perform processes related to managing, prioritizing, and scheduling multiple pending tasks. For example, app(s) 254 may configure computer terminal 140 to perform operations including receiving input of task information, displaying pending tasks, monitoring task status, assigning tasks to employees, and displaying employee task assignments.

Figure 3:
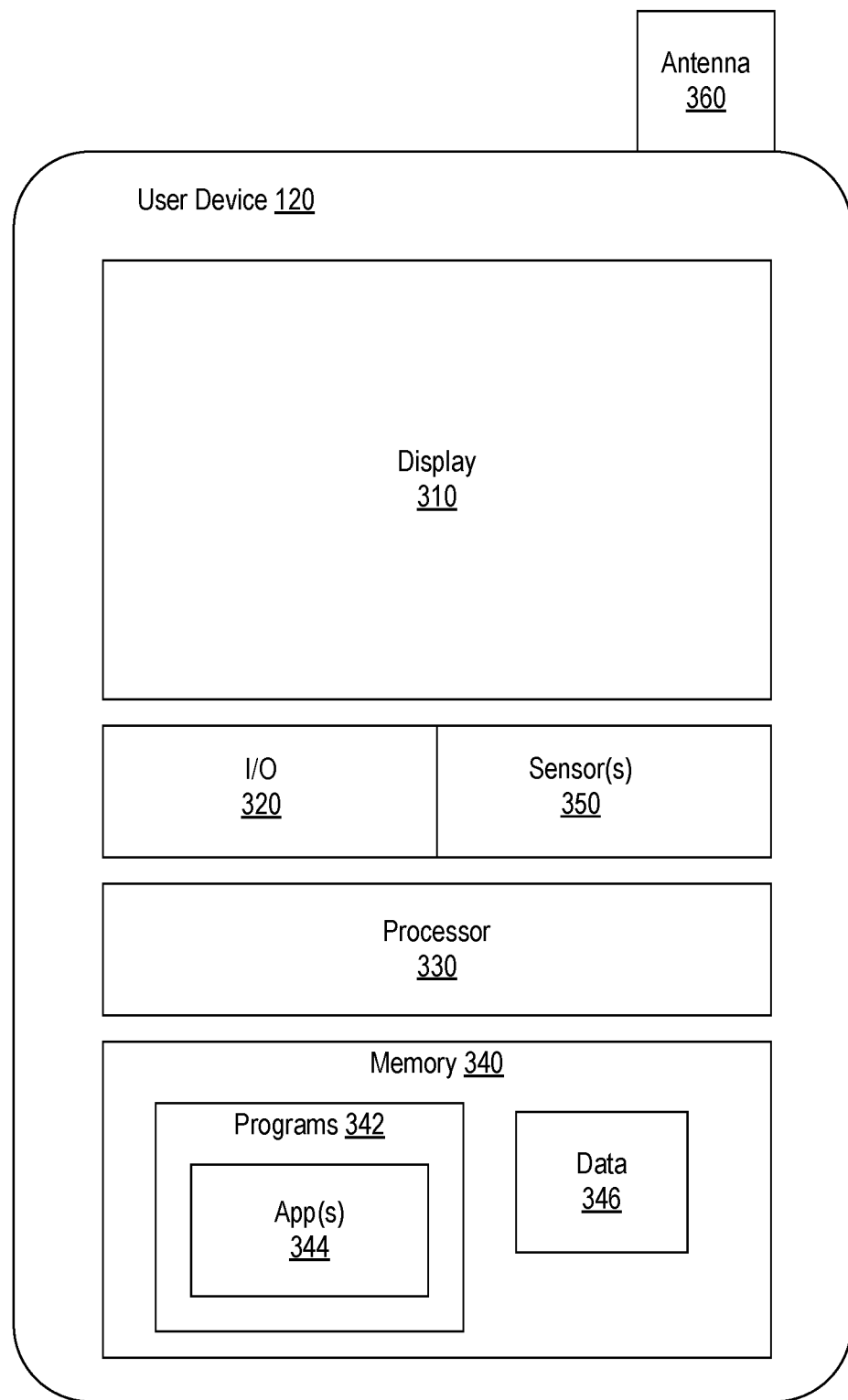
FIG. 3 depicts an example of a user device, consistent with embodiments of the present disclosure.

FIG. 3 shows a diagram of an exemplary user device 120, consistent with disclosed embodiments. As shown, user device 120 may include display 310, I/O device(s) 320, processor 330, memory 340 having stored thereon data 346 and one or more programs 342, such as app(s) 344, sensor(s) 350, and antenna 360.

Display 310 may include one or more devices for displaying information, including but not limited to, liquid crystal displays (LCD), light emitting diode (LED) screens, organic light emitting diode (OLED) screens, and other known display devices.

I/O devices 320 may include one or more devices that allow mobile device 120 to send and receive information. I/O devices 320 may include, for example, a pointing device, keyboard, buttons, switches, and/or a touchscreen panel. I/O devices 320 may also include one or more communication modules (not shown) for sending and receiving information via antenna 360 from other components in system 100 by, for example, establishing wired or wireless connectivity between mobile device 120 to local network 110, network 150, or by establishing direct wired or wireless connections between user device 120 and other components of system 100. Direct connections may include, for example, Bluetooth™, Bluetooth™ LE, WiFi, near field communications (NFC), or other known communication methods which provide a medium for transmitting data between separate devices.

Processor(s) 330 may be one or more known computing devices, such as those described with respect to processor 220 in FIG. 2.

Memory 340 may be a volatile or non-volatile, magnetic, semiconductor, tape, optical, removable, non-removable, or other type of storage device or tangible (i.e., non-transitory) computer-readable medium such as those described with respect to memory 250 in FIG. 2.

In some embodiments, user device 120 may contain one or more sensors 350 for collecting environmental, movement, and/or security data. Sensors 350 may include: one or more environmental sensors such as, for example, ambient light sensors, microphones, temperature sensors, and humidity sensors; motion detectors such as, for example, GPS receivers, location-based data receivers, accelerometers, and gyroscopes; and security sensors such as, for example, fingerprint readers, retina scanners, and other biometric sensors capable of use for security and individual identification. In some embodiments, processor 330 may use data collected by sensors 350 to control or modify functions of program(s) 342.

Figure 4:
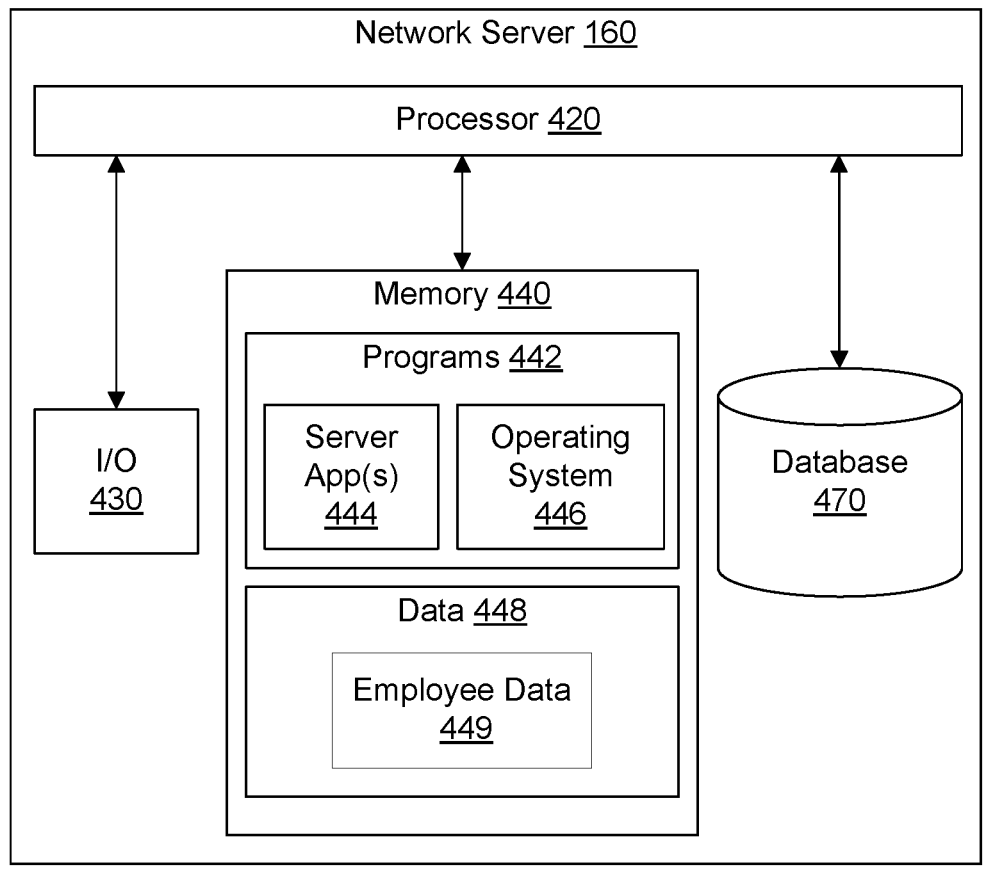
FIG. 4 depicts an example of a network server, consistent with embodiments of the present disclosure.

FIG. 4 shows a diagram of an exemplary network server 160, consistent with disclosed embodiments. In some embodiments, network server 160 may support or provide a cloud computing service, such as Microsoft Azure or Amazon Web Services. In such embodiments, network server 160 may include one or more distributed computer systems capable of performing distributed computing functions and providing cloud computing services and functions consistent with disclosed embodiments. In some embodiments, network server 160 may operate in conjunction with facility server 130. In other embodiments, network server 160 may operate alone, and facility server 130 may be replaced by a network connection to network 150 and/or local network 110. In such embodiments, network server 160 may perform all functions associated with the disclosed methods. In other embodiments, facility server 130 may operate alone, without network server 160. In such embodiments, facility system 102 may operate as a standalone system, in which facility server 130 performs all functions associated with the disclosed methods. Those of ordinary skill in the art will appreciate that the computing arrangements are not limited to these examples, and that other embodiments may include one or more alternate configurations of computing systems capable of performing functions associated with the disclosed embodiments.

In some embodiments, network server 160 may connect to multiple facilities located in different geographical locations. In such embodiments, network server 160 may manage tasks that span across multiple facilities, such as a request for an equipment item to be transported between facilities. Additionally, network server 160 may collect data from multiple facilities to evaluate performance times in different facilities, and improve the accuracy of expected completion times for different types of tasks using one or more data regression algorithms.

As shown in FIG. 4, network server 160 may include one or more processor(s) 420, input/output ("I/O") devices 430, memory 440 storing programs 442 (including, for example, server app(s) 444 and operating system 446) and data 448, and a database 470. Network server 160 may be a single server or may be configured as a distributed computer system including multiple servers or computers that interoperate to perform one or more of the processes and functionalities associated with the disclosed embodiments.

Processor(s) 420 may be one or more known computing devices, such as those described with respect to processor 220 in FIG. 2.

In some embodiments, network server 160 may also include one or more I/O devices 430 including interfaces for receiving signals or input from devices and providing signals or output to one or more devices that allow data to be received and/or transmitted by network server 160. For example, network server 160 may include interface components, which may provide interfaces to one or more input devices, such as one or more keyboards, mouse devices, and the like, that enable network server 160 to receive input from one or more user 125 that is associated with facility system 102.

In some embodiments, network server 160 may include one or more storage devices configured to store information used by processor 420 (or other components) to perform certain functions related to the disclosed embodiments. In one example, network server 160 may include memory 440 that includes instructions to enable processor 420 to execute one or more applications, such as server applications, an electronic transaction application, an account status application, network communication processes, and any other type of application or software known to be available on computer systems. Alternatively or additionally, the instructions, application programs, etc. may be stored in an internal database 470 or external database 180 (shown in FIG. 1) in communication with network server 160, such as one or more database or memory accessible over network 150. Database 470 or other external storage may be a volatile or non-volatile, magnetic, semiconductor, tape, optical, removable, non-removable, or other type of storage device or tangible (i.e., non-transitory) computer-readable medium.

In one embodiment, network server 160 may include memory 440 that includes instructions that, when executed by processor 420, perform one or more processes consistent with the functionalities disclosed herein. Methods, systems, and articles of manufacture consistent with disclosed embodiments are not limited to separate programs or computers configured to perform dedicated tasks. For example, network server 160 may include memory 440 that may include one or more programs 442 to perform one or more functions of the disclosed embodiments. Moreover, processor 420 may execute one or more programs located remotely from account information display system 100. For example, network server 160 may access one or more remote programs, that, when executed, perform functions related to disclosed embodiments.

Programs 450 stored in memory 440 and executed by processor(s) 420 may include one or more server app(s) 452 and operating system 454. Server app(s) 452 may incorporate one or more apps configured to receive input of task information, display pending tasks, monitor task status, assign tasks to employees, and display employee task assignments.

In some embodiments, memory 440 may store data 448 including data associated with employees, tasks, assets, assignment algorithms, and any other data related to the disclosed embodiments. For example, data 448 may include one or more entries including identifications of employees, their skill sets, their schedules and availability, employee locations (expected locations/posts, and real-time locations), and tasks assigned to each employee. Data 448 may also include one or more entries including attributes related to task priority levels, task durations, task origin and destination locations, asset items associated with tasks, asset locations associated with tasks, employee information for employees that previously performed particular tasks, and any other data related to task attributes, task requirements, and task performance. Data 448 may include information related to previous tasks, pending tasks, scheduled tasks, and expected or forecasted tasks. Data 448 may be stored relative to particular tasks, as aggregate statistical data, or any other means or organization. In some embodiments, data 448 is stored in database 470, memory 440, memory 250, memory 340, database 180, and any combination thereof.

In some embodiments, memory 440 and database 470 may include one or more memory devices that store data and instructions used to perform one or more features of the disclosed embodiments. Memory 440 and database 470 may also include any combination of one or more databases controlled by memory controller devices (e.g., server(s), etc.) or software, such as document management systems, Microsoft SQL databases, SharePoint databases, Oracle databases, Sybase databases, or other relational databases.

Network server 160 may communicate with one or more remote memory devices (e.g., third-party server 170 and/or database 180) through network 150 or a different network (not shown). The remote memory devices may be configured to store information and may be accessed and/or managed by network server 160. By way of example only, the remote memory devices may be document management systems, Microsoft SQL database, SharePoint databases, Oracle™ databases, Sybase™ databases, or other relational databases. Systems and methods consistent with disclosed embodiments, however, are not limited to separate databases or even to the use of a database.

Figure 5:
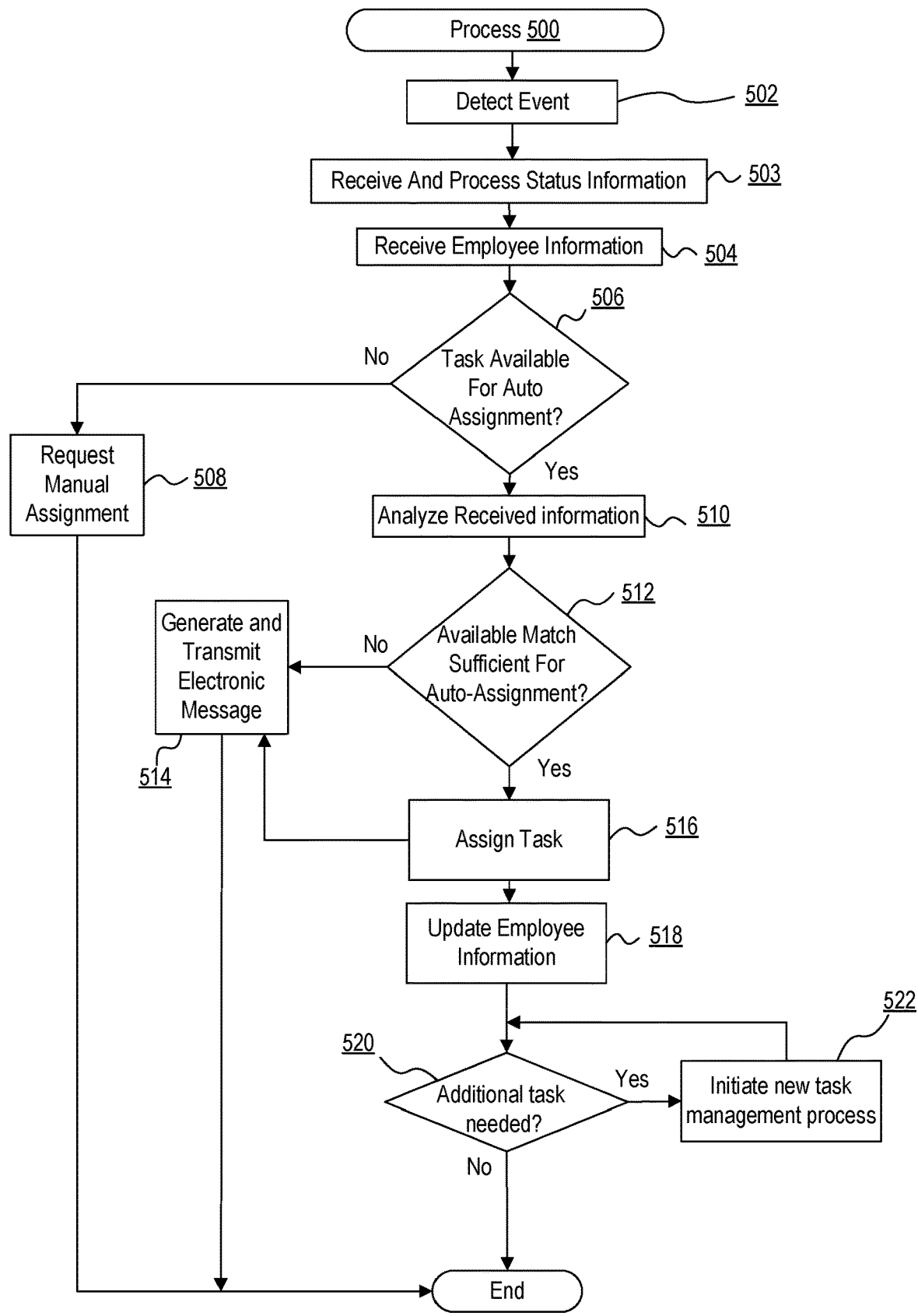
FIG. 5 is a flowchart of an example of a process for detecting events within a facility and communicating task information, consistent with embodiments of the present disclosure.

FIG. 5 shows a flowchart of an exemplary process 500 for detecting events within a facility and communicating task information. Process 500 is described herein as performed primarily by network server 160, however in some embodiments, facility server 130, computer terminal 140, administration terminal 145, user device 120, and/or third party server 170 may perform one or more steps of process 500.

Process 500 may begin in step 502 when network server 160 detects an event within the facility. In some embodiments, network server 160 may detect an event in response to receipt of monitoring information from one or more networked devices. In some embodiments, monitoring information may comprise sensor data collected by one or more networked sensor devices. In some embodiments, monitoring information may include a task request from a terminal such as computer terminal 145, administration terminal 145, and/or user device 120. In some embodiments, task requests may include a text message, email, communication from app 254 or 344, or other written request from any electronic device in communication with network server 160. In some embodiments, network server 160 may receive one or more task requests via another interface, such as an interactive voice response (IVR) system, or touch-tone phone entry system. Network server 160 may process the received task information to extract one or more attributes about the task. In some embodiments, network server 502 may determine whether multiple pending requests are associated with a similar location, task, and/or equipment or supplies.

In some embodiments, network server 160 may detect events in response to collected data from one or more sensors located within the facility, or one or more sensor devices associated with individuals such as employees or patients in the facility. For example, network server 160 may detect an event associated with a patient arriving to a particular location in a hospital, or traveling toward a particular location in the hospital. As another example, sensor data associated with equipment in the facility may be indicative of an alert or warning requiring intervention.

Network server 160 may further process the task request to determine associated requirements. For example, network server 160 may process the task request to determine labor requirements associated with the task. In such embodiments, network server 160 may determine whether multiple employees are necessary for completion of the task or whether multiple similar tasks may be grouped together into a batch, to be performed by a single employee (not shown in figures). In some embodiments, network server 160 may even determine whether a task that is already assigned to another employee is in progress and, if not, network server 160 may unassign the task dynamically and include the unassigned task in a batch of tasks for a single employee. Thus, network server 160 may identify an efficient manner for completing pending tasks using fewer employees, when appropriate.

Network server 160 may further process the task request to determine requirements related to facilities, equipment, or other resources. For example, in some embodiments, network server 160 may process the task to determine whether a particular type of room is necessary for completion of the task or to determine an expected range of time for completion of the task.

In step 503, network server 160 may receive and process status information. The received status information may include information related to availability of resources within a facility such as rooms, equipment, transportation, or other status information. The status information may be real-time information, historical information, projected information, or any combination.

In step 504, network server 160 may receive employee information, such as employee data 449 retrieved from any of memory 440. In some embodiments, network server 160 may determine which employees are currently available based on, for example, one or more work schedules or computer entries indicating that the employee is presently at the facility and working. In some embodiments, a work schedule may indicate one or more times that the employee is scheduled to begin working and finish working. Network server 160 request and receive employee information for the employees that are available at the time of the task request.

In some embodiments, network server 160 may retrieve employee information from database 180, or from any other memory associated with components of system 100. In some embodiments, employee information may include one or more attributes associated with the employees of the facility For example, employee information may include a job title, certifications, qualifications, skill sets, dates and times scheduled to work, expected location of work, expected current location, detected current location, tasks currently assigned to the employee, a status of the assigned tasks, and performance data related to previous tasks.

In some embodiments, employee location may include a room, department, or area of a facility assigned to the employee in a work schedule, a manual entry from the employee, a detected location based on locating equipment, or any other means of designating an employee's location within a facility. In some embodiments, employee location may include coordinates such as latitude and longitude, distance from particular landmark in the facility, or one or more designations of locations in the facility, such as buildings, floors, units, zones and/or room numbers. Employee location may include both a designation of a specific location and one or more designations of more general location (e.g., room and zone).

In some embodiments, employee information may include a history of tasks that the employee has performed, and one or more statistics associated with the employee's performance of the tasks. For example, employee information may include information identifying completed tasks, date and time of task assignment (start time) and completion (end time), and other historical information regarding past tasks.

In step 506, network server 160 may determine if the requested task is eligible for automatic assignment to one or more employees. For example, network server 160 may determine whether the requested task is associated with one or more predetermined categories of tasks that are eligible for automatic assignment. In some embodiments, network server 160 may store categories of tasks that are suitable for automatic assignment, and task categories that are unavailable for automatic assignment due to safety considerations, or task categories that include factors not yet integrated into the rule sets integrated within network server 160.

If the task is ineligible for automatic assignment ("no" in step 506), process 500 may proceed to step 508, in which network server 160 generates a notification to request manual assignment of the task. In some embodiments, the generated notification may appear as an alert on one or more of user device 120, computer terminal 140, and/or administration terminal 145. For example, in some embodiments, network server 160 may send an email or text message to an appropriate user 125, to request manual assignment of the new task. Upon receiving a manual assignment of the new task, process 500 may end. In some embodiments, network server 160 may create and/or update one or more database entries for employee information and task information, to reflect the manual task assignment.

If network server 160 determines that the new task is available for automatic assignment ("yes" in step 506), then in step 510 network server 160 may analyze task information for the requested task along with received employee information. Step 510 is described in further detail with respect to FIG. 6.

In step 512, network server 160 may determine whether at least one employee matches the requested task, and whether the results of step 510 include one or more matches suitable for auto-assignment. In some embodiments, network server 160 may evaluate one or more matches produced in step 510. If no matches are suitable for auto-assignment ("no" in step 512), in step 514 network server 160 may generate one or more notifications that an automatic assignment was not possible, based on the received task information and available employees. Similar to step 508, the notifications may appear as an alert on one or more component of system 100, such as user device 120, computer terminal 140, or administration terminal 145. In some embodiments, network server 160 may generate an email or text message to an individual and/or device outside of facility system 102 (not shown in figures).

If network server 160 identifies at least one suitable employee match for auto-assignment to the task ("yes" in step 512), then in step 516 network server 160 may assign the task to one or more employees. Step 516 is described in further detail with respect to FIG. 7A.

In step 518, network server 160 may update employee information to reflect the task assignment. In some embodiments, network server 160 may create and/or update one or more database entries with the updated employee information immediately, or nearly immediately. In some embodiments, network server 160 may also generate one or more alerts to notify one or more employees of the updated employee information, via one or more components of system 100. For example, network server 160 may generate an alert notifying a responder employee that that a new task is assigned to them. In some embodiments, network server 160 may generate one or more alerts to requester employee(s), to inform the requester(s) that the task is assigned to a responder employee. Network server 160 may send such notifications to user device 120, administration terminal 145, and/or computer terminal 140.

In step 520, network server 160 may determine whether the assigned task may necessitate additional tasks. For example an assigned task such as admitting a patient or moving a patient from one type of hospital room to another type of room may require completion of certain tasks upon assignment, prior to completion of the task, or soon after completion of the task. If no additional tasks are necessary ("no" in step 520), process 500 may end.

As another example, a task for cleaning a patient room may not be able to begin until curtains are removed, rather than relying on an employee waiting for curtain removal to request it, at step 520 network server may determine that cleaning requires curtain removal and that curtain removal has not yet occurred.

Alternatively, if one or more additional tasks are necessary ("yes" in step 520), in step 522 network server 160 may initiate a new task management process related to the task. The additional task may be assigned using through task management process 500, for example through a new instance of task management process 500 for the additional task starting at step 502. After initiation of the new task management process for the additional task, task management process 500 may proceed back to step 520 to determine if any further tasks are necessary in association with the assigned task. Steps 520 and 522 are described in further detail with respect to FIG. 8.

In some embodiments, network server 160 may create and/or update one or more database entries including task information for the newly assigned task (not shown in figure). For example, network server 160 may store a database entry identifying the task, a request time, an assignment time, an employee identification of the requestor(s), an employee identification of the dispatcher (if any), an employee identification of the responder(s), an origin location of the task, a destination location of the task, any assets, equipment, food, medicine, or other supplies associated with the task, an expected completion time, and any custom comments associated with the task received from one or more of the requestor, dispatcher, and respondent. In some embodiments, stored employee and task database entries may be accessible to users 125 including requestors, dispatchers, and responders via one or more of mobile device 120, computer terminal 140, and/or administration terminal 145.

Figure 6:
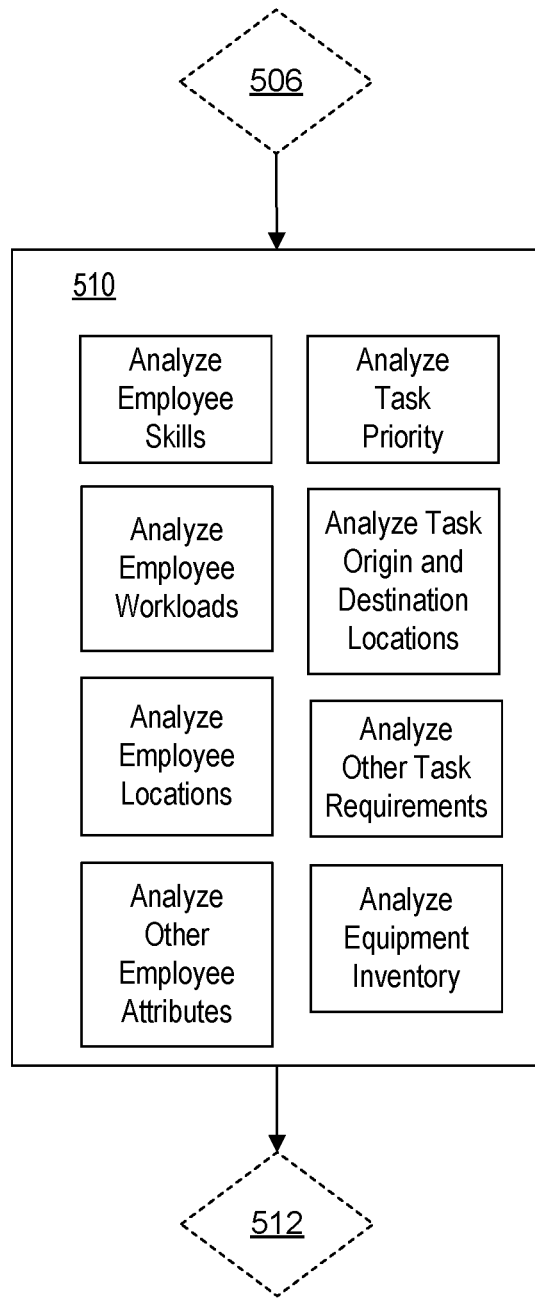
FIG. 6 is a flowchart of an example of a process for comparing task information and employee information, consistent with embodiments of the present disclosure.

FIG. 6 is a flowchart of an example of a process for step 510 of analyzing task information and employee information. As shown in FIG. 6, network server 160 may analyze a plurality of factors during step 510, to identify one or more matches between employees and the task information. Network server 160 may perform one or more analyses of step 510 in parallel or in varying sequences, depending on the needs of the requestor, dispatcher, or the facility. In some embodiments, network server 160 may score the results of each analysis, to generate a numerical score that may be used to rank available employees for selection. In some embodiments, each analysis may be weighted, depending on the priorities and needs of the facility, of a requester or dispatcher, or of a facility administrator. Step 510 may also include more or fewer analyses depending on the types of available employee information, and attributes included in the task information.

In some embodiments, network server 160 may analyze employee skills. For example, network server 160 may determine the skill sets and/or certifications associated with each available employee. Skill sets and certifications may include indications entered manually by the employee's supervisor, trainer, or other authority figure. In some embodiments, network server 160 may automatically store skill sets and/or certifications in association with employees, based on previously completed tasks.

In some embodiments, network server 160 may compare employee skills and certifications to one or more task requirements. For example, network server 160 may determine whether a requested task requires any particular skill sets and/or certifications, and filter the available employees based on this determination. In some embodiments, network server 160 may rank available employees based on a quantity of relevant skill sets and/or certifications, so that the most qualified employees for the task are prioritized over lesser-qualified employees.

In some embodiments, network server 160 may analyze employee workloads. For example, network server 160 may determine how many tasks are currently assigned to each employee, compared to a total number of tasks that may be assigned to the employee at any given time. In such embodiments, network server 160 may distribute tasks in an equitable manner, so maintain an equal number of tasks assigned to each employee at any given time, within a predetermined tolerance. Thus, network server 160 may distribute tasks to employees who have fewer than the average or median number of tasks for all employees. In some embodiments, network server 160 may assign tasks in a "round robin" fashion, by rotating task assignments according to a determined or predefined order.

In some embodiments, network server 160 may determine a task assignment rotation or predefined order among a subset of employees having a particular skill set or performance level, thereby providing even distribution of tasks among a group of individuals with the appropriate skills.

In some embodiments, a total number of tasks may include a manual database entry from an administrator or supervisor. In other embodiments, network server 160 may automatically and dynamically determine a total number of tasks that can be assigned to the employee at any given time, based on prior performance statistics and workloads. For example, if network server 160 determines that employee A previously handled 4 tasks simultaneously in a timely manner without any problems, network server 160 may automatically increase employee A's total number of tasks to 5 tasks. In some embodiments, network server 160 may rank available employees according to a number or percentage of available task slots, so that employees with fewer currently assigned tasks are prioritized for assignment over employees who have full or nearly-full current workloads.

In some embodiments, network server 160 may analyze employee locations. For example, network server 160 may determine an expected location for each employee, based on the employee's job title, job assignment, work schedule, or other database entry identifying an expected location for the employee. In some embodiments, employees may wear one or more electronic tags that can transmit a location signal to network server 160. In such embodiments, network server 160 can maintain a database of each available employee's real-time location in the facility. In some embodiments, user device 120 may include one or more location sensors, and user device 120 may transmit a real-time location signal to server 160, to provide a current location of an employee associated with the user device 120.

In some embodiments, network server 160 may compare employee locations to one or more locations associated with a requested task, such as the task origin location, task destination location, and one or more locations of equipment and supplies associated with the requested task. As an example, network server 160 may determine which employees are currently located, or are expected to be located, closest to a location whether the requested task originates. For example, if a requested task involves moving a bariatric hospital bed from supply room A to patient room 100, network server 160 may determine which available employees are currently located in closest proximity to supply room A, where the moving task originates. As another example, if the requested task indicates that a second employee is required to set up the bariatric bed in patient room 100 (but that only a single employee is needed to move the bed to patient room 100), then network server 160 may identify one or more available employees currently located closest to the task destination location (patient room A), to assign as the second employee for the task. In some embodiments, network server 160 may rank available employees based on proximity to the origin and/or destination locations for the task.

In some embodiments, network server 160 may analyze other employee attributes and other task requirements. For example, network server 160 may determine whether any available employees have restrictions or disabilities that may prevent them from being able to perform the requested task. Additionally, network server 160 may determine whether employees are scheduled to be on a break, or are located in a location of the facility associated with a break period, lunch period, or other location that may affect the employee's availability status for the task.

In some embodiments, network server 160 may analyze a priority of the requested task. In some embodiments, task priority may be indicated manually by the requestor and/or dispatcher when the task request is created. In other embodiments, network server 160 may assign a priority level to the task based on one or more stored rule sets that may take into account factors such as, a requested time frame for completing the task, the nature or type of task, a location of the task (such as an emergency room or operating room), and any other factors related to an indication or urgency or importance. In some embodiments, network server 160 may attempt to assign high priority tasks to employees associated with more skills and certifications, employees who do not currently have any assigned tasks and can begin a high priority task immediately, or employees who have historically handled high priority tasks within a predetermined time frame and without errors.

In some embodiments, network server 160 may analyze one or more attributes regarding assets associated with the requested task such as equipment and/or supplies. For example, network server 160 may determine an inventory level of required equipment and/or supplies, a location of the equipment and/or supplies, instructions associated with the equipment and/or supplies, and required certifications or skills associated with the equipment and/or supplies. In some embodiments, network server 160 may determine a location of the assets based on one or more database entries indicating an expected location (such as a supply room) of the assets. In other embodiments, assets may be tagged with one or more electronic devices for broadcasting a location, condition, and inventory level of certain assets, and network server 160 may determine a real-time location, inventory level, and condition of each tagged asset. In some embodiments, network server 160 may compare the attributes to employee attributes such as, for example, employee location, employee skill sets and certifications, prior experience with certain equipment and/or supplies, and any other attributes related to the equipment and/or supplies, in order to identify one or more employees that match the equipment attributes. In some embodiments, network server 160 may rank or score the available employees based on a quantity or amount of matching or compatible attributes between the employee attributes and equipment attributes.

At the completion of step 510, network server 160 may create a ranked list of available employees based on one or more scores and/or rankings of individual analyses. In some embodiments, network server 160 may assign a weighting to one or more of the scores and/or ratings for each analysis, based on the needs of the requestor, dispatcher, and/or the facility. In some embodiments, weightings for different analyses may be stored as a rule set and accessed by network server 160 during step 510.

Figure 7A:
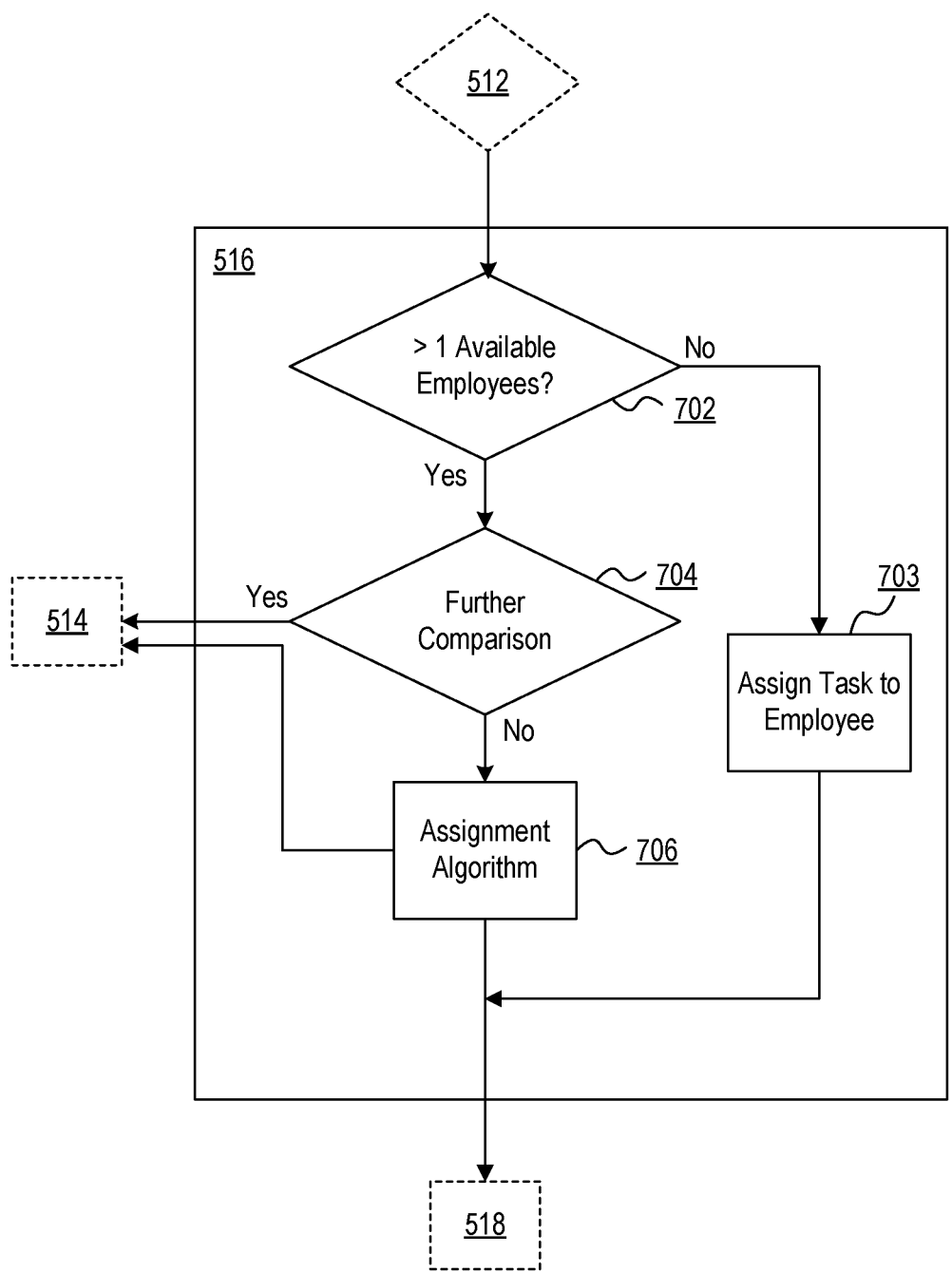
FIG. 7A is a flowchart of an example of a process for assigning a task to an employee, consistent with embodiments of the present disclosure.

FIG. 7A is a flowchart of an example process for identifying an available match sufficient for auto-assignment 512 that may take place as a part of process 500. As shown, in step 702, network server 160 may determine whether there is more than 1 employee identified in step 510 that matches task requirements and attributes. If only one employee is identified ("no" in step 702), then in step 703 network server 160 may automatically assign the task to the single identified employee. Network server 160 may then proceed to step 518 (of process 500, shown in FIG. 5). If more than 1 employee was identified in step 510 ("yes" in step 702), then in step 704 network server 160 may determine whether further comparison is required before assigning an employee to the requested task. For example, if multiple employees are ranked and/or scored equally (an example determination of "yes" in step 704), then process 500 may proceed to step 514 in which network server 160 may generate one or more notifications and request input from a dispatcher for assigning the task. In some embodiments, network server 160 may determine whether further comparison can be conducted to further narrow the number of potential employees for assignment of the task. For example, while one or more attributes may be sufficient for a match if only one employee is available with those attributes, a more optimized match may be sought if additional employees are available. In such embodiments, step 510 may apply a first set of filters and rules to narrow down a pool of potential employees, and in step 704 network server 160 may determine whether a second set of filters and/or rules should be applied to the remaining pool of potential employees, to identify a targeted list of employees. In some embodiments, in step 704 network server 160 may determine whether a threshold number of potential employees is exceeded, indicating a need for additional comparison. If further comparison is to be applied ("yes" in step 704), process 500 may return to step 510 (not illustrated in FIG. 7A).

If network server 160 determines that further comparison is not required, then in step 706 network server 160 may apply one or more assignment algorithms for assigning the requested task to one or more employees. In some embodiments, network server 160 may implement a round-robin type of assignment algorithm, in which network server 160 cycles through a pre-ordered list of available employees that match the task requirements and attributes, and network server 160 may continue assigning tasks to the next employee listed, until the employee's workload capacity is reached (e.g., the total number of task slots for a particular employee are filled). In some embodiments, network server 160 may identify a highest ranked or highest scored employee, based on the results of step 510, and attempt to assign the task to that employee. If the employee becomes unavailable or refuses to accept the task, then network server 160 may assign the task to the next-highest ranked/scored employee, until the task is accepted and started. In other embodiments, network server 160 may employ one or more other assignment algorithms for assigning tasks to employees that take into account an employee availability, employee workload and skill set, and attributes of the requested task. Once the task is assigned, network server 160 may automatically generate and transmit information associated with a message to the assigned individual or employee, such as in step 514. In some embodiments, network server 160 may generate instructions for automatically displaying a graphical user interface on a mobile device screen associated with the assigned employee. Such messages and notifications are described in further detail with respect to FIG. 10. After assigning the task, process 500 may proceed to step 518 (shown in FIG. 5).

In some embodiments, network server 160 may reevaluate existing task assignments to promote an even distribution of work among active employees. Network server 160 may be configured to periodically evaluate workload disparities among employees and, if necessary, automatically reassign tasks to reduce such disparities. For example, network server 160 may compare the number of tasks assigned to an employee to the number of tasks assigned to other employees, or to an average number of tasks currently assigned to active employees. If the difference is greater than a predetermined threshold, network server 160 may use process 500 to automatically reassign tasks, reducing the difference. Other means of quantifying workload, such as expected time to complete the task, may be used to determine whether tasks should be reassigned. Automatic task reassignment may occur on a real-time, ongoing basis, on a schedule, periodically (e.g., every hour), or based on the occurrence of predetermined events which could indicate a disparity or potential disparity in workload. Such events could include, for example, an employee becoming active or inactive or a particular number of manual task assignments being received within a given period of time.

Figure 7B:
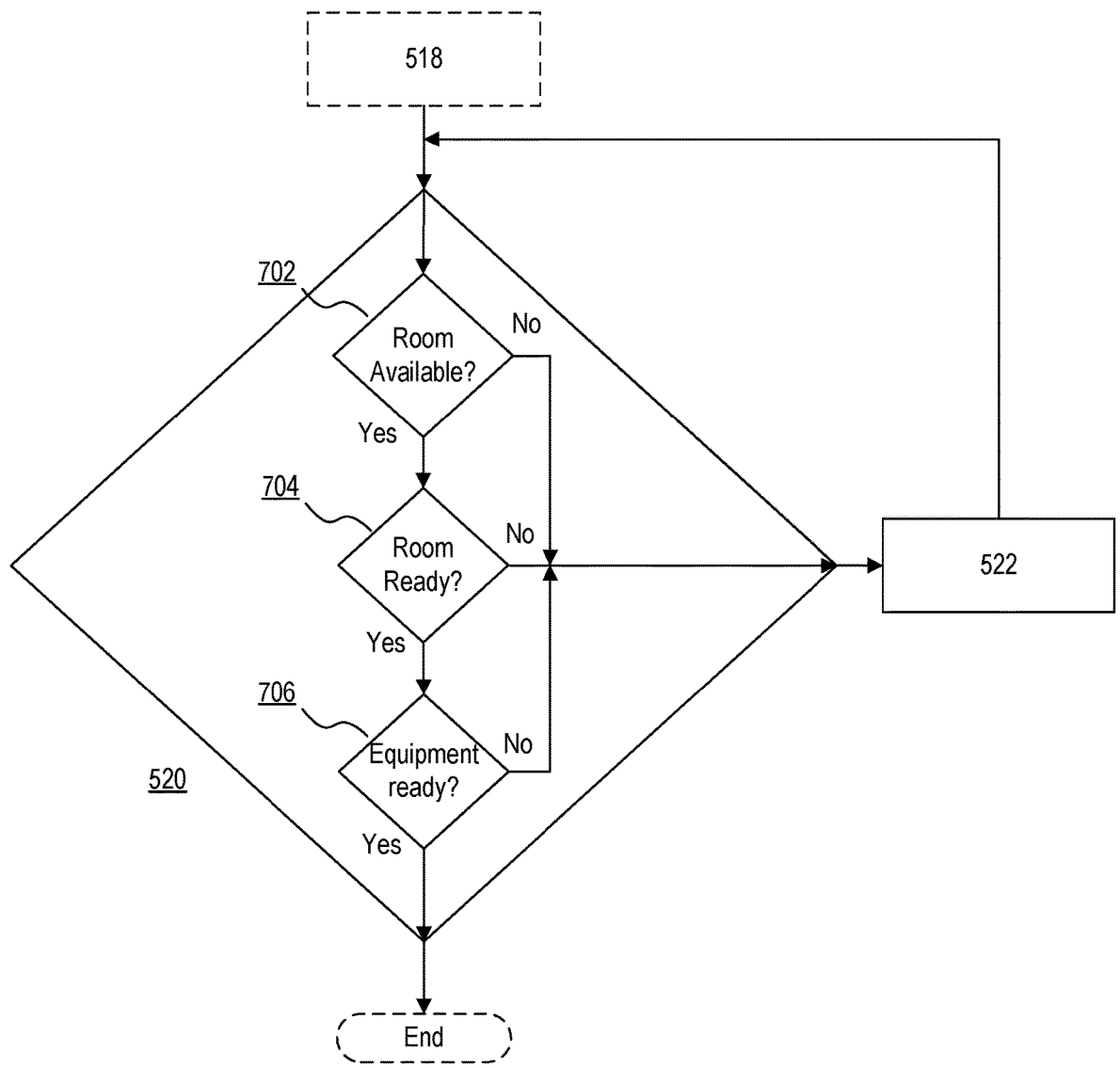
FIG. 7B is a flowchart of an example of a process for automated task scheduling and management, consistent with embodiments of the present disclosure.

FIG. 7B is a flowchart of an example process for determining whether an assigned task may necessitate additional tasks such as in step 520 of FIG. 5. As shown, network server 160 may make a series of determinations as a part of determining whether to initiate a new task. For example, in steps 702, 704, and, 706, network server may determine room availability, room status, and whether any necessary equipment is ready, respectively. Such determinations may be based on a bill of materials associated with the assigned task, and may vary based on any number of requirements.

If any of the determinations of step 520 indicate a further task is needed, network server 160 may proceed to step 522. In step 522, network server may create a new task request for processing via task management process 500. The task request may incorporate information associated with the assigned task. For example, if an assigned task involves a transfer of a patient from one type of room to another, network server 160 may determine in step 520 that a room requires cleaning in order to complete the transfer. In such a case, in step 522, network server 160 may initiate a new task request including a requirement that the task is completed prior to an expected time of completion of the patient transfer. As a further example, equipment may be needed in a room to which the assigned task is scheduled to transfer a patient. The equipment may not be needed immediately after the patient arrives in the room, but instead within a certain time period after. Accordingly in step 522, network server 160 may initiate a new task request including a requirement that the task is completed prior to a period of time after an expected time of completion of the patient transfer.

FIG. 8 is an illustration of an example of a task management interface 800, consistent with disclosed embodiments. Task management interface 800 may be displayed, for example, at computer terminal 140 or administrator terminal 145 based on communication over local network 110 and/or network 150. An administrator or other employee responsible for overseeing task management may interact with administrator terminal 145 in order to operate task management interface 800. Task management interface 800 may include a list of tasks active in system 100, and employee list 806 that includes a number of assigned and completed tasks associated with each employee. In some embodiments, employee list 806 may indicate one or more statuses for each employee such as, for example, whether an employee is "available" (e.g., on duty and not working on any task), "dispatched" (e.g., on duty and currently working on a task), or "logged out" (e.g., off duty). In some embodiments, employee list 806 may display more or fewer statuses depending on the types of data collected and the needs of the facility and its administrators. In other embodiments, employee list 806 may indicate a number of tasks that a particular employee has completed, out of the total number of tasks assigned during the employee's time on duty.

In some embodiments, the list of tasks in task management interface 800 may be organized based on task attributes 802, such as creation date and time, progress status, task identification number, task category, associated assets such as equipment and/or supplies, task priority, associated departments, origin location and/or destination location associated with the task. Other attributes that may be associated with a task will be apparent to those of skill in the art.

In some embodiments, task management interface 800 may provide a real-time status of each pending task in the facility, or a particular department of the facility. For example, when the facility is a medical facility, task management interface 800 may display all tasks for a particular department such as maintenance, housekeeping, food service, medical equipment delivery, medical transport, and any other support departments or teams within the medical facility. In some embodiments, one or more administrative terminals 145 may display a task management interface 800 that displays all tasks for the entire medical facility.

In some embodiments, task management interface 800 may provide a real-time status for each task based on continuously collected data from one or more of user device 120, computer terminal 140, administrative terminal 145, one or more tracking devices such as real time locating system (RTLS) tags, one or more sensors located throughout the facility such as proximity sensors, temperature sensors, presence sensors, door and room access sensors, and manual inputs via IVR or other manual entry systems. In some embodiments, network server 160 may receive real-time data streams associated with the status of a task, including indications from users 125 via user device 120 that a task is started, completed, delayed, or that a milestone of the task is completed. In some embodiments, network server 160 may track a duration of each task in progress, and determine an expected completion time for each task based on a plurality of factors such as, for example, an average historical time to complete a similar type of task, the assigned employee's current workload and historical timeliness rating, indications of potential or confirmed delays based on input from the assigned employee, and any other factors relevant to an expected duration and/or completion time of the task. In some embodiments, task management interface 800 may display an expected completion time for each task, elapsed duration for each task, and expected or confirmed length of delay for each task.

In some embodiments, task management interface 800 may provide, upon request via interface 800, additional details for particular tasks including, for example, details for completion or progress of each step of the task since the task began up to the current time (real-time). In some embodiments, interface 800 may provide or more configurable alerts to the task requester and/or dispatcher, if the employee does not complete the task within a predetermined period of time, or if the employee is determined to be in a location of the facility that is inconsistent with the pending assigned task.

In some embodiments, an additional window or popup window (not shown in figures) may appear displaying details for a particular task including a creation time, a time of assignment, a time that the assigned employee began the task, a time of reassignment (if any), times and durations of delays, a completion time of task steps, and any other milestones that are associated with one or more timestamps.

In some embodiments, task management interface 800 may include a button for creating a new task, such as interface element 804. Upon receiving a selection of interface element 804, network server 160 may generate information for displaying task creation interface 900, as illustrated in FIG. 9.

Figure 9:
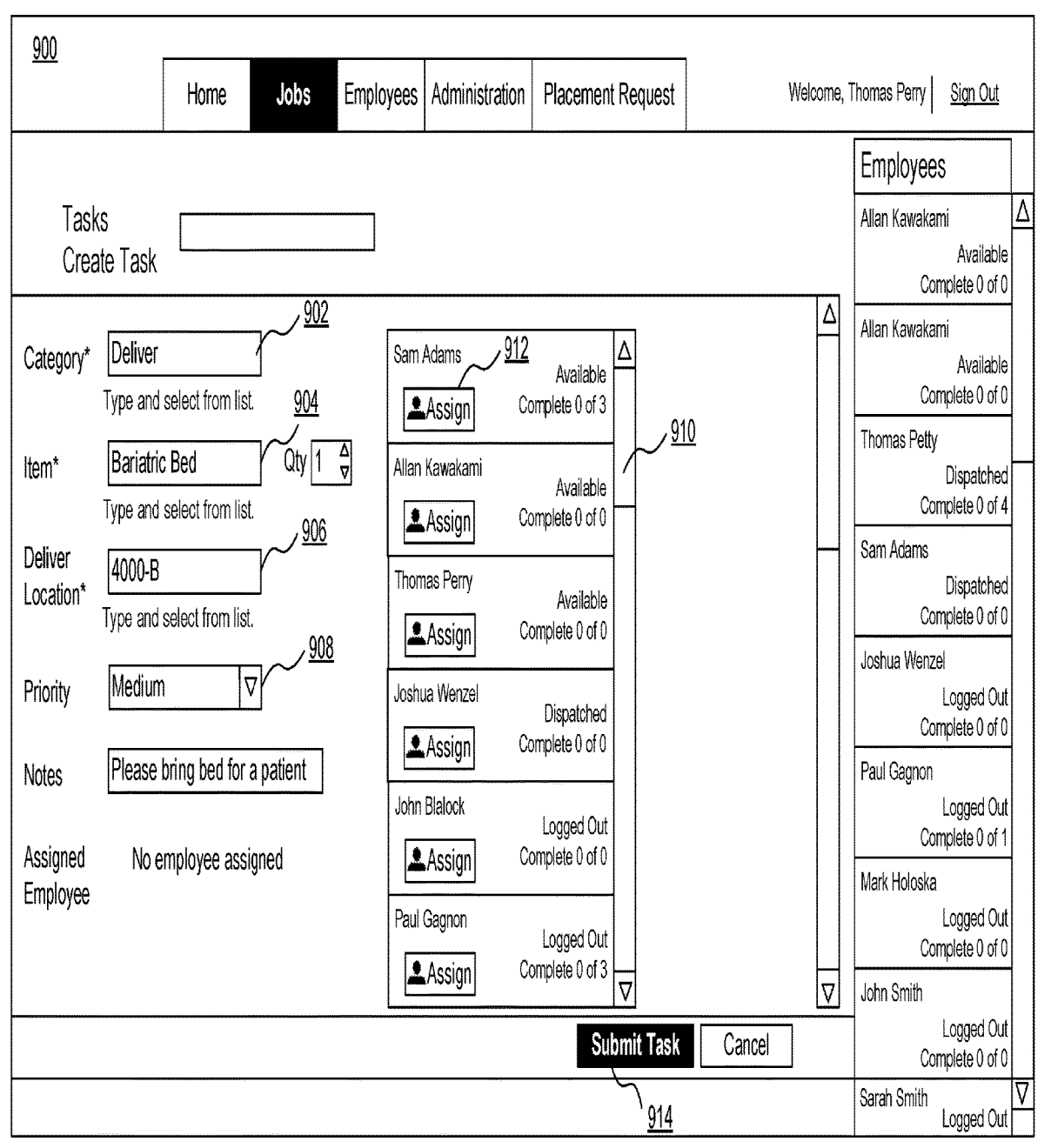

FIG. 9 is an illustration of a task creation interface 900, consistent with disclosed embodiments. Task creation interface 900 may allow a user 125 (such as a requestor and/or dispatcher) to create a customized task request with specific instructions for the responder. In some embodiments, interface 900 may include options for specifying the full details of the task such as, for example, the type of task, origin location, destination location, and equipment and/or supplies associated with the task. In some embodiments, network server 160 may access one or more database entries that associate predetermined tasks with one or more of origin and destination locations, equipment and/or supplies, equipment and/or supply locations, equipment and/or supply quantities, priority levels, required skills and/or certifications, and any other attributes which can be stored in association with one or more tasks. In such embodiments, a requestor or dispatcher may only need to identify the task requested, a task location, a desired start time, and/or a desired completion time. Thus, network server 160 may automate significant aspects of the process for requesting a task and assigning the task, streamlining communication, management, workload distribution, and efficiency in the facility. In a facility such as a hospital, such improvements may significantly increase quality of care by shortening response times and increasing an amount of time and effort that caregivers can provide to patients rather than generating requests, following-up on requests, and handling other aspects of task requests that are usually delegated to respondents.

In some embodiments, task creation interface 900 may include one or more detail fields 902, 904, 906, and 908 to allow a requester or dispatcher to specify one or more attributes associated with a new task, such as attributes 802 of FIG. 8. In some embodiments, one or more of details fields 902, 904, 906, or 908 may populate automatically based on selections for one or more of the other fields. For example, interface 900 may include field 902 for entry of a task category. Interface 900 may also include field 904 for entry of an item, such as a piece of equipment, associated with the task. Interface 900 may also include field 906 for entry of a location associated with the task. In some embodiments, interface 900 may include field 908 for entry of a priority associated with the task.

Embodiments consistent with the current disclosure may include additional or alternative fields as a part of interface 900. Furthermore, one or more fields included in new task interface 900 may be generated sequentially or dynamically as information is entered, such that additional fields may be displayed based on entries in previously displayed fields. In some embodiments, network server 160 may automatically populate one or more of fields 904, 906, or 908 based on a task category selected in field 902. For example, if a requestor selects "infusion pump delivery" for field 902, network server 160 may automatically determine where infusion pumps are stored, an inventory and maintenance condition of the stored infusion pumps, and automatically populate a field indicating the infusion pump location. Network server 160 may automatically select another infusion pump storage location once the requestor identifies the destination location for the infusion pump, to select a storage location that is closest to the destination location. Upon creating the new task, network server 160 may determine which employee(s) are available that are located closest to the infusion pump storage location, are qualified to handle infusion pumps, and have at least one task slot available to deliver the infusion pump by the requested time or within an average expected delivery time.

In some embodiments, interface 900 may include list 910 displaying potential employees for assignment of the new task. List 910 may include all employees, employees available for assignment of a new task, or only those employees which meet criteria identified in task attribute entry fields. In some embodiments, the employees and/or ranking of employees in list 910 may change dynamically in response to each field input. In some embodiments, list 910 may include a button for manually assigning one or more employees to a new task, such as interface element 912, in association with one or more of the employees in list 910. In response to a selection of one or more interface elements 912, network server 160 may assign the new task to the employee associated with the selected interface element 912.

In some embodiments, new task interface 900 may include a button for submitting the new task, such as interface element 914. Upon receiving a selection of interface element 914, network server 160 may finalize entry of the new task and execute process 500 to assign the task to one or more employees.

In some embodiments, interfaces 800 and/or 900 may be tailored based on any number of circumstances or attributes at the time of use. For example, network server 160 may determine, based on attributes related, for example, to an associated facility or an employee interacting with interface 800, whether to make interface element 804 available. For example, workload, location, schedule, past performance, and other factors may be used. As a more specific example, network server may determine that an employee with a schedule that is occupied beyond a particular percentage of capacity may not create new tasks. Alternatively, an employee may be manually barred from creating new tasks. Based on the determination that the employee is not permitted to create a new task, interface 800 may not show interface element 804 or may display it in a way that indicates it cannot be selected (e.g., "greyed out").

Further, based on any of the factors described above, or others, an employee may be restricted as to who they can assign a task. For example, list 910 may display only names of other employees that report to that supervisor. As another example, an employee may be barred from assigning tasks to themselves, and as a result, his or her own name may not appear in list 910. Such restrictions may be constant, or may be based on schedule, performance, number of outstanding assigned tasks, or other factors.

Figure 10:
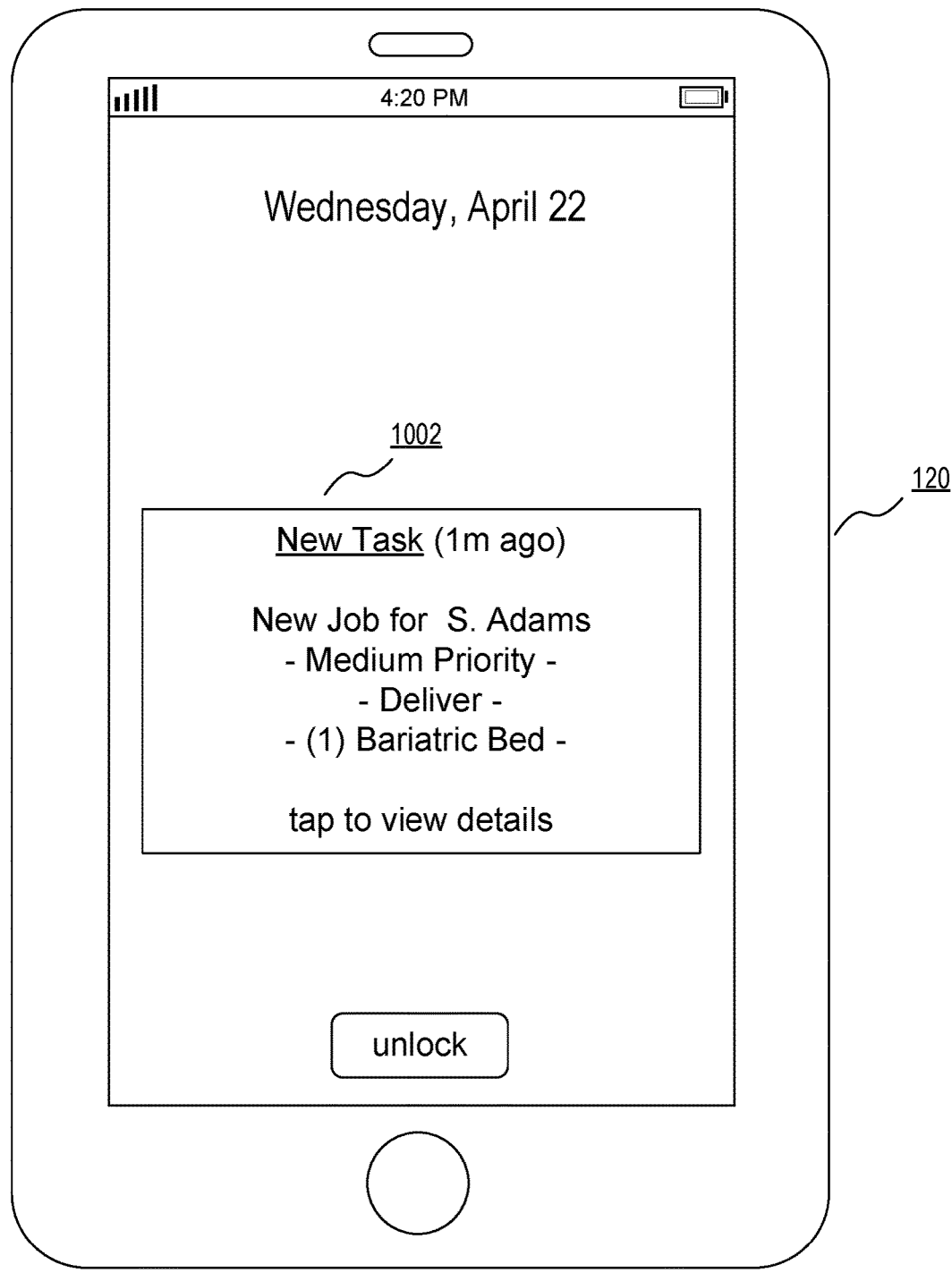
FIGS. 10 and 11 are illustrations of examples of task notification and management interfaces, consistent with embodiments of the present disclosure.

FIG. 10 is an illustration of an example of a task notification interface 1000. Display 310 of user device 120 may display interface 1000 in response to instructions from network server 160, to alert a responder that a new task is assigned to them. Interface 1000 may include a notification box 1002, to provide essential details of the task assignment. Notification box 1002 may include some or all of the attributes 802 included in the task assignment, depending on the settings of app 252 and the space available on display 310. In the example shown, notification box 102 may include, for example, a time that the new task was assigned, a priority level, a category of the task, and equipment and/or supplies associated with the task.

In some embodiments, network server 160 may transmit instructions for displaying notification box 1002 to user device 120 via any means of data transmission discussed above or known in the art. For example, network server 160 may transmit instructions for notification box 1002 via network 150 to local network 110 of facility system 102. Alternatively, network server 160 may transmit notification 1002 via a network other than network 150, such as a cellular or satellite communication system. In some embodiments, network server 160 may instruct third party server 170 to generate and transmit instructions for displaying notification box 1002. In such embodiments, third party server 170 may be operated by a notification service such as Apple notifications, Android notifications, or Blackberry notifications. In such embodiments, third party server 170 may receive instructions from network server 160, and then transmit instructions for displaying notification box 1002 to user device 120.

In some embodiments, network server 160 may transmit instructions for notification box 1002 via other communication means such as, for example, SMS message, a recorded audio message delivered via plain old telephone service (POTS), or to a provider of paging services.

Figure 11:
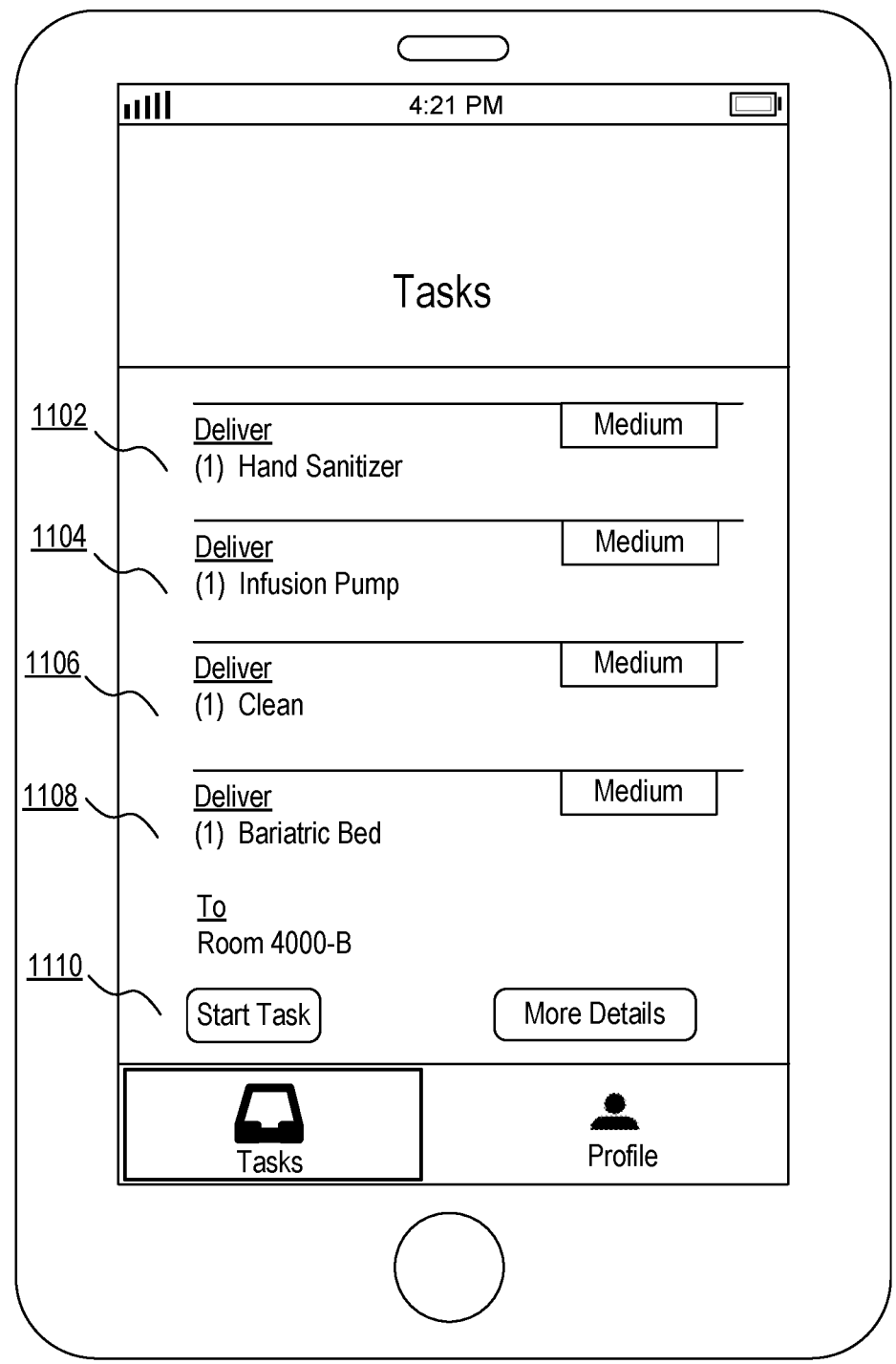

FIG. 11 is an illustration of a task management interface 1100. Display 310 of user device 120 may display interface 1100 in response to instructions received from network server 160. In some embodiments, app 252 may generate and display interface 1100 based on the received instructions. User 125 may enable mobile task management interface 1100 by interacting with notification box 1002 (in FIG. 10), or by navigating through one or more interfaces of app 252 to display assigned tasks.

In some embodiments, interface 1100 may display tasks assigned to an employee such as user 125, such as tasks 1102, 1104, 1106, and 1108. Tasks 1102, 1104, 1106, and 1108 may include some or all of the attributes 602 associated with each task.

In some embodiments, interface 1100 may include a button such as interface element 1110 which, when selected, notifies network server 160 that the employee has started working on the task. In response to selection of interface element 1110 by user 125, user device 120 may instruct network server 160 to update employee information (e.g. employee data 449 of network server 160) to reflect that user 125 has begun the task. Network server 160 may then update one or more database entries associated with the employee and the task. In some embodiments, network server 160 may generate and transmit one or more notifications to any interested parties such as, for example, the task requestor and/or dispatcher, indicating that the assigned employee is working on the task.

In some embodiments, app 252 may include one or more interfaces (not shown in figures) for entering information related to task progress, task completion, and/or delays. For example, while working on a task, an employee such as user 125 may select one or more interface elements in an interface generated by app 252 to indicate that a step of the task is complete. Upon selection of the interface element, app 252 may cause user device 120 to inform network server 160 that a step of the task has been completed, and a timestamp of the step completion. In some embodiments, selection of one or more interface elements may inform network server 160 that one or more steps of the task cannot be completed in the estimated time frame and by the expected completion time. For example, if a supply room having necessary equipment is locked or blocked, or if a necessary piece of equipment is unexpectedly damaged, then the employee may indicate via app 252 that one or more steps cannot be completed on time. In some embodiments, selection on an interface element may indicate that the step must be delayed for an estimated time period, such as 30 minutes or an hour.

In some embodiments, selection of another interface element may indicate that the step must be suspended, i.e. delayed indefinitely. In response, network server 160 may unassign the task and queue the task for reevaluation and reassignment at a later time. For example, if an employee arrives at a storage room to find that the only available infusion pump is damaged beyond immediate repair, the employee may suspend the task. In some embodiments, the employee may manually indicate that the task should be suspended and reassigned at a later time. In other embodiments, network server 160 may automatically suspend the task, if the employee delays the task with a delay time that exceeds a predetermined threshold such as, for example, 3 hours. Network server 160 may unassign the task from the employee, and attempt to reassign the task after a predetermined time period. In some embodiments, network server 160 may also automatically generate a new task for repairing the infusion pump and/or an emergency request to transport an infusion pump from another facility. Network server 160 may determine an estimated time for transporting and/or repairing the infusion pump, and attempt to reassign the infusion pump delivery task upon completion of the transport/repair task, to the another employee identified using process 500. Thus, in some embodiments network server 160 may automatically identify the need for additional tasks based on occurrences or conditions that arise in current tasks. In such situations, network server 160 may automatically generate the additional tasks based on the detected occurrences and/or conditions, and automatically assign the additional tasks to the proper employees using process 500.

Network server 160 may also automatically create additional tasks at the time of task creation and/or assignment via process 500. For example, if at step 502, network server 160 receives task information for a task that requires an item, network server 160 may determine whether the item is available or present at an expected location. If the item is not present or is otherwise unavailable, network server 160 may create a new task for delivering the item. As noted above, network server 160 may delay, unassign, or reassign the task requiring the item, based on the timing involved in delivering the item.

In some embodiments, network server 160 may automatically generate and assign tasks according to a predetermined schedule, or in response to one or more trigger conditions. As a first example, network server 160 may receive, from a requestor, or dispatcher, a schedule for restocking a medicine storage room every 7 days. Network server may automatically assign the recurring task according to the schedule, to the correct employee for the task given current workload conditions and employee availabilities. In some embodiments, the medicine storage room may include one or more inventory level sensors, to detect an inventory of medicine containers and/or doses remaining in storage. Network server 160 may determine if the inventory level drops below a predetermined threshold, and create and assign one or more tasks based on the detected inventory level. In some embodiments, sensor devices disposed throughout the facility may include necessary processing capabilities and logic to compare sensed conditions (such as an inventory level) to one or more predetermined thresholds, and transmit a task request to network server 160 upon detecting that a predetermined threshold is exceeded.

As a second example, network server 160 may monitor one or more trigger conditions, such as a temperature sensor in a cold medicine storage room. If the detected temperature exceeds a predetermined threshold, network server 160 may automatically generate a high priority task to investigate the failed temperature control. Network server 160 may execute process 500 to determine which employees are currently available with the proper skill set to investigate and/or repair the cold storage room, determine which employees have a low workload to address the high priority task, and which employees are closest to the cold storage room and/or a room with the necessary diagnostic and repair tools. After considering these and other necessary factors, network server 160 may identify one or more employees suitable and available for the task, and generate instructions for providing a notification box 1002 for the task on the selected employee's user device 120. In some embodiments, network server 160 may update one or more database entries to identify the selected employee as assigned to the task.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware, firmware, and software, but systems and methods consistent with the present disclosure can be implemented as hardware alone.

Computer programs based on the written description and methods of this specification are within the skill of a software developer. The various programs or program modules can be created using a variety of programming techniques. For example, program sections or program modules can be designed in or by means of Java, C, C++, assembly language, or any such programming languages. One or more of such software sections or modules can be integrated into a computer system, non-transitory computer-readable media, or existing communications software.

Moreover, while illustrative embodiments have been described herein, the scope includes any and all embodiments having equivalent elements, modifications, omissions, combinations (e.g., of aspects across various embodiments), adaptations or alterations based on the present disclosure. Further, the steps of the disclosed methods can be modified in any manner, including by reordering steps or inserting or deleting steps.

What is claimed is:

1. A method, the method comprising:
   receiving, at a centralized server and from one or more of a plurality of wireless sensors distributed through a healthcare facility, monitoring information, wherein the receiving is responsive to the centralized server dynamically and automatically querying the one or more sensors for real-time sensor data;
   determining the real-time sensor data exceeds one or more predetermined thresholds;
   responsive to the determining the real-time sensor data exceeds the one or more predetermined thresholds, identifying, by analyzing the monitoring information, a task to be performed, requirements of the task, and that the task is eligible for automatic assignment, wherein identifying the task is eligible for automatic assignment comprises utilizing at least one rule set that identifies whether the task is eligible for automatic assignment and that assigns a priority to the task;
   receiving, at the centralized server and from the one or more of the plurality of wireless sensors, a current location of each of a plurality of individuals detected by the one or more of the plurality of wireless sensors from a signal received from at least one of one or more locating tags operatively coupled to one or more of the plurality of individuals in proximity to the plurality of wireless sensors;
   automatically assigning the task, wherein the automatically assigning comprises unassigning the task from an already assigned one of a plurality of individuals responsive to determining the task has not yet been started by the one of the plurality of individuals, each of the plurality of individuals associated with a mobile device comprising a display and executing a mobile application displaying task assignments, wherein the automatically assigning comprises:
      identifying a plurality of matches of the task to more than one of the plurality of individuals by matching the task to the more than one of the plurality of individuals based on attributes of the individuals, the requirements of the task, and the priority of the task;
      ranking each of the matches based upon a ranking rule set factoring in a number of available task slots for an individual, a priority of the task, a quantity of skills corresponding to the task of the individual, and a proximity of the individual to the task based on the received current location of the individual, and iteratively performing the identifying a plurality of matches and ranking each of the matches based upon additional task and individual attributes upon identifying a number of the plurality of matches exceeds a predetermined threshold; and
      in response to identifying the plurality of matches, automatically assigning the task to one of the more than one of the plurality of individuals, wherein the one of the more than one of the plurality of individuals corresponds to one of the plurality of matches having a highest ranking within the plurality of matches;
   generating instructions to automatically display a graphical user interface (GUI) within the mobile application of the mobile device associated with the one of the more than one of the plurality of individuals, displaying a notification that the task has been assigned to the one of the more than one of the plurality of individuals, wherein the notification displays details and attributes of the task, wherein a number of attributes displayed within the notification is based upon an amount of space available on the display of the mobile device;
   determining one or more additional tasks are related to the task and automatically assigning the one or more additional tasks to one or more individuals, wherein automatically assigning the one or more additional tasks comprises grouping the one or more additional tasks with the task and assigning the grouped tasks to one of: the one of the more than one of the plurality of individuals or another of the plurality of individuals, wherein assigning the grouped tasks to another of the plurality of individuals comprises automatically unassigning the task from the one of the more than one of the plurality of individuals;
   updating at least one GUI of the mobile device associated with the individual with the assignment of the task and the one or more additional tasks;
   receiving a selection of a GUI button, displayed on the mobile device associated with the one of the more than one of the plurality of individuals or the another of the plurality of individuals assigned to the task, to start the task; and
   updating, in response to receiving the selection of the GUI button to start the task, a database entry, within a networked database coupled to the centralized server, to indicate the task has started.

2. The method of claim 1, wherein the one or more sensors comprising at least one of environmental sensors, motion detectors, or security sensors.

3. The method of claim 1, comprising determining a number of employees needed for performing the task by analyzing the task.

4. The method of claim 3, wherein the automatically assigning comprises automatically assigning the task to a number of employees matching the number of employees needed for performing the task.

5. The method of claim 1, wherein the automatically assigning comprises determining the task is eligible for automatic assignment by determining a category of the task and identifying the category corresponds to a category eligible for automatic assignment.

6. The method of claim 1, wherein the plurality of matches are ranked based upon scores assigned to each of the plurality of matches, wherein the scores are assigned based upon a quantity of matching attributes between the task and a corresponding individual.

7. The method of claim 1, wherein:
the identifying the plurality of matches comprises:
applying a first set of filters to the information about the plurality of individuals to generate a pool of individuals;
applying a second set of filters to the pool to identify a highly targeted list of individuals; and
employing a round-robin assignment based on the highly targeted list to identify the mobile device associated with the one of the plurality of individuals automatically assigned to the task.

8. The method of claim 1, comprising determining resource requirements of the task by analyzing the task.

9. The method of claim 1, wherein the identifying a plurality of matches comprises identifying the one of the plurality of individuals is currently available.

10. The method of claim 1, comprising generating an alert corresponding to the task assignment on the display within the mobile application associated with the individual.

11. A system, the system comprising:
a plurality of mobile devices, each associated with one of a plurality of individuals, each of the mobile devices comprising a display and executing a mobile application;
a networked database;
one or more of a plurality of wireless sensors distributed through a healthcare facility; and
a central communication server coupled to the one or more sensors and the networked database via a wireless network, the central communication server comprising:
a memory storing instructions; and
at least one processor configured to execute the stored instructions to:
receive, at the central communication server and from the one or more of the plurality of wireless sensors, monitoring information, wherein the receiving is responsive to the central communication server dynamically and automatically querying the one or more sensors for real-time sensor data;
determine the real-time sensor data exceeds one or more predetermined thresholds;
responsive to the determining the real-time sensor data exceeds the one or more predetermined thresholds, identify, by analyzing the monitoring information, a task to be performed, requirements of the task, and that the task is eligible for automatic assignment, wherein identifying the task is eligible for automatic assignment comprises utilizing at least one rule set that identifies whether the task is eligible for automatic assignment and that assigns a priority to the task;
receive, at the central communication server and from the one or more of the plurality of wireless sensors, a current location of each of a plurality of individuals detected by the one or more of the plurality of wireless sensors from a signal received from at least one of one or more locating tags operatively coupled to one or more of the plurality of individuals in proximity to the plurality of wireless sensors;
automatically assign the task, wherein the automatically assigning comprises unassigning the task from an already assigned one of a plurality of individuals responsive to determining the task has not yet been started by the one of the plurality of individuals, each of the plurality of individuals associated with one of the plurality of mobile devices, wherein the automatically assigning comprises:
identifying a plurality of matches of the task to more than one of the plurality of individuals by matching the task to the more than one of the plurality of individuals based on attributes of the individuals, the requirements of the task, and the priority of the task;
ranking each of the matches based upon a ranking rule set factoring in a number of available task slots for an individual, a priority of the task, a quantity of skills corresponding to the task of the individual, and a proximity of the individual to the task based on the received current location of the individual, and iteratively performing the identifying a plurality of matches and ranking each of the matches based upon additional task and individual attributes upon identifying a number of the plurality of matches exceeds a predetermined threshold;
in response to identifying the plurality of matches, automatically assigning the task to one of the more than one of the plurality of individuals, wherein the one of the more than one of the plurality of individuals corresponds to one of the plurality of matches having a highest ranking within the plurality of matches;
generate instructions to automatically display a graphical user interface (GUI) within the mobile application of the mobile device associated with the one of the more than one of the plurality of individuals, displaying a notification that the task has been assigned to the one of the more than one of the plurality of individuals, wherein the notification displays details and attributes of the task, wherein a number of attributes displayed within the notification is based upon an amount of space available on the display of the mobile device;
determine one or more additional tasks are related to the task and automatically assigning the one or more additional tasks to one or more individuals, wherein automatically assigning the one or more additional tasks comprises grouping the one or more additional tasks with the task and assigning the grouped tasks to one of: the one of the more than one of the plurality of individuals or another of the plurality of individuals, wherein assigning the grouped tasks to another of the plurality of individuals comprises automatically unassigning the task from the one of the more than one of the plurality of individuals;
update at least one graphical user interface GUI of the mobile device associated with the individual with the assignment of the task and the one or more additional tasks;
receive a selection of a GUI button, displayed on the mobile device associated with the one of the more than one of the plurality of individuals or the another of the plurality of individuals assigned to the task, to start the task; and update, in response to receiving the selection of the GUI button to start the task, a database entry, within the networked database coupled to the central communication server, to indicate the task has started.

12. The system of claim 11, wherein the one or more sensors comprising at least one of environmental sensors, motion detectors, or security sensors.

13. The system of claim 11, comprising determining a number of employees needed for performing the task by analyzing the task.

14. The system of claim 13, wherein the automatically assigning comprises automatically assigning the task to a number of employees matching the number of employees needed for performing the task.

15. The system of claim 11, wherein the automatically assigning comprises determining the task is eligible for automatic assignment by determining a category of the task and identifying the category corresponds to a category eligible for automatic assignment.

16. The system of claim 11, wherein the plurality of matches are ranked based upon scores assigned to each of the plurality of matches, wherein the scores are assigned based upon a quantity of matching attributes between the task and a corresponding individual.

17. The system of claim 11, wherein:
the identifying the plurality of matches comprises:
applying a first set of filters to the information about the plurality of individuals to generate a pool of individuals;
applying a second set of filters to the pool to identify a highly targeted list of individuals; and
employing a round-robin assignment based on the highly targeted list to identify the mobile device associated with the one of the plurality of individuals automatically assigned to the task.

18. The system of claim 11, wherein the identifying a plurality of matches comprises identifying the one of the plurality of individuals is currently available.

19. The system of claim 11, comprising generating an alert corresponding to the task assignment on the display within the mobile application associated with the individual.

20. A product, the product comprising:
a non-transitory computer-readable storage device that stores executable code that, when executed by a processor, causes the product to:
receive, at a centralized server and from one or more of a plurality of wireless sensors distributed through a healthcare facility, monitoring information, wherein the receiving is responsive to the centralized server dynamically and automatically querying the one or more sensors for real-time sensor data;
determine the real-time sensor data exceeds one or more predetermined thresholds;
responsive to the determining the real-time sensor data exceeds the one or more predetermined thresholds, identify, by analyzing the monitoring information, a task to be performed, requirements of the task, and that the task is eligible for automatic assignment, wherein identifying the task is eligible for automatic assignment comprises utilizing at least one rule set that identifies whether the task is eligible for automatic assignment and that assigns a priority to the task;
receive, at the centralized server and from the one or more of the plurality of wireless sensors, a current location of each of a plurality of individuals detected by the one or more of the plurality of wireless sensors from a signal received from at least one of one or more locating tags operatively coupled to one or more of the plurality of individuals in proximity to the plurality of wireless sensors;
automatically assign the task, wherein the automatically assigning comprises unas signing the task from an already assigned one of a plurality of individuals responsive to determining the task has not yet been started by the one of the plurality of individuals, each of the plurality of individuals associated with a mobile device comprising a display and executing a mobile application displaying task assignments, wherein the automatically assigning comprises:
identifying a plurality of matches of the task to more than one of the plurality of individuals by matching the task to the more than one of the plurality of individuals based on attributes of the individuals, the requirements of the task, and the priority of the task;
ranking each of the matches based upon a ranking rule set factoring in a number of available task slots for an individual, a priority of the task, a quantity of skills corresponding to the task of the individual, and a proximity of the individual to the task based on the received current location of the individual, and iteratively performing the identifying a plurality of matches and ranking each of the matches based upon additional task and individual attributes upon identifying a number of the plurality of matches exceeds a predetermined threshold;
in response to identifying the plurality of matches, automatically assigning the task to one of the more than one of the plurality of individuals, wherein the one of the more than one of the plurality of individuals corresponds to one of the plurality of matches having a highest ranking within the plurality of matches;
generate instructions to automatically display a graphical user interface (GUI) within the mobile application of the mobile device associated with the one of the more than one of the plurality of individuals, displaying a notification that the task has been assigned to the one of the more than one of the plurality of individuals, wherein the notification displays details and attributes of the task, wherein a number of attributes displayed within the notification is based upon an amount of space available on the display of the mobile device;
determine one or more additional tasks are related to the task and automatically assigning the one or more additional tasks to one or more individuals, wherein automatically assigning the one or more additional tasks comprises grouping the one or more additional tasks with the task and assigning the grouped tasks to one of: the one of the more than one of the plurality of individuals or another of the plurality of individuals, wherein assigning the grouped tasks to another of the plurality of individuals comprises automatically unassigning the task from the one of the more than one of the plurality of individuals;
update at least one graphical user interface GUI of the mobile device associated with the individual with the assignment of the task and the one or more additional tasks;
receive a selection of a GUI button, displayed on the mobile device associated with the one of the more than one of the plurality of individuals or the another of the plurality of individuals assigned to the task, to start the task; and update, in response to receiving the selection of the GUI button to start the task, a database entry, within a networked database coupled to the centralized server, to indicate the task has started.

\* \* \* \* \*